ns Patent [19]

Edwards

[11] 4,001,421
[45] Jan. 4, 1977

[54] THIAZOLE CARDIOVASCULAR AGENTS
[75] Inventor: John A. Edwards, Los Altos, Calif.
[73] Assignee: Syntex (U.S.A.) Inc., Palo Alto, Calif.
[22] Filed: Mar. 27, 1975
[21] Appl. No.: 562,718

Related U.S. Application Data

[60] Division of Ser. No. 451,179, March 14, 1974, Pat. No. 3,897,441, which is a continuation-in-part of Ser. No. 289,730, Sept. 15, 1972, Pat. No. 3,850,945, which is a continuation-in-part of Ser. No. 193,172, Oct. 27, 1971, abandoned, which is a continuation-in-part of Ser. No. 343,945, March 22, 1973, abandoned.

[52] U.S. Cl. .................. 424/270; 424/248.51; 424/250; 424/263; 424/267; 424/274
[51] Int. Cl.$^2$ ..................... A61K 31/425
[58] Field of Search .......... 424/270, 248, 250, 263, 424/267, 274

[56] References Cited

UNITED STATES PATENTS

| | | | |
|---|---|---|---|
| 3,328,417 | 6/1967 | McLoughlin et al. | 260/302 R |
| 3,715,369 | 2/1973 | Possgit et al. | 260/302 R |
| 3,803,160 | 4/1974 | Bosshard et al. | 260/302 R |
| 3,803,161 | 4/1974 | Wgi | 260/306.8 R |
| 3,833,727 | 9/1974 | Nelson et al. | 424/270 |
| 3,932,400 | 1/1976 | Hibino et al. | 424/270 |

OTHER PUBLICATIONS

Physician's Desk Reference (PDR), 1974, pp. 580–582.

Primary Examiner—Norman A. Drezin
Attorney, Agent, or Firm—Lawrence S. Squires; William B. Walker

[57] ABSTRACT

1-Amino-3-(4- or 5-substituted thiazol-2-oxy)-2-propanol and/or substituted amino derivatives thereof; 3-(4- or 5-substituted thiazol-2-oxy)-1,2-epoxypropane and 5-(4- or 5-substituted thiazol-2-oxymethylene)-oxazolidine and/or N- and/or 2-substituted oxazolidine derivatives thereof, are methods of making such compounds. The compounds are characterized by an aminocarbonyl or carbonylamino type substituent at the 5- or 4-position on the thiazole ring. The above 1-amino-3-(4- or 5-substituted thiazol-2-oxy)-2-propanol and derivatives exhibit cardiovascular activity and are useful in the treatment of abnormal heart conditions in mammals. The 3-(4- or 5-substituted thiazol-2-oxy)-1,2-epoxypropanes are useful as intermediates for the aforementioned cardiovascular agents. The 5-(4- or 5-substituted thiazol-2-oxymethylene)-oxazolidine and derivatives are intermediates for the aforementioned cardiovascular agents and further exhibit cardiovascular activity and thus are useful in the treatment of abnormal heart conditions in mammals. The 1-amino-3-(4-or 5-substituted thiazol-2-oxy)-2-propanol and derivatives can be prepared by base or acid hydrolysis of the corresponding 5-(4- or 5-aminocarbonylthiazol-2-oxymethylene)-oxazolidine or derivative; or by treatment of the corresponding 3-(4- or 5-substituted thiazol-2-oxy)-2,3-epoxypropane or derivative with the desired amine or amine derivative.

6 Claims, No Drawings

THIAZOLE CARDIOVASCULAR AGENTS

CROSS REFERENCE TO RELATED APPLICATIONS

This application is a division of U.S. Ser. No. 451,179, filed Mar. 14, 1974, now U.S. Pat. No. 3,987,441, which is a continuation-in-part of U.S. Ser. No. 289,730, filed Sept. 15, 1972, now U.S. Pat. No. 3,850,945, which in turn is a continuation-in-part of U.S. Ser. No. 193,172, filed Oct. 27, 1971, and now abandoned; and of U.S. Ser. No. 343,945, filed Mar. 22, 1973, and now abandoned, which is also a continuation-in-part of U.S. Ser. No. 289,730, filed Sept. 15, 1972, which in turn is a continuation-in-part of application Ser. No. 193,172, filed Oct. 27, 1971.

BACKGROUND OF THE INVENTION

1. Field of the Invention

This invention relates to 3-(4- or 5-substituted thiazol-2-oxy)-propane derivatives and 4'- or 5'-substituted thiazol-2-oxymethylene-oxazolidine derivatives and to methods of preparing such compounds. In a further aspect this invention relates to 1-amino-3-(4- or 5-substituted thiazol-2-oxy)-2-propanol and 1-(substituted amino)- and/or 4'- or 5 '-substituted thiazole derivatives thereof and to methods of preparing such compounds. In a still further aspect this invention relates to 3-(4- or 5-substituted thiazol-2-oxy)-1,2-epoxypropane derivatives and to methods of preparing and using such compounds. In another aspect this invention relates to 4'- or 5'-substituted thiazol-2'-oxy-methylene-oxazolidine derivatives thereof and to methods of preparing and using compounds. This invention also relates to pharmaceutical compositions comprising the 1-amino-3-(4- or 5-substituted thiazol-2-oxy)-2-propanol and derivatives, of the invention, and/or the 4'- or 5'-substituted thiazol-2-oxy-methylene oxazolidine and derivatives, of the invention, and to methods of applying such compositions for the treatment of mammals.

2. THE PRIOR ART

At the present time, the compound frequently used in the United States for the treatment of several cardiac arrhythmias is propranolol (i.e. 1-(isopropylamino)-3-(1-naphthyloxy)-2-propanol). This compound primarily achieves its therapeutic action by blocking cardiac β-adrenergic receptor sites and is a general β-adrenergic blocker which blocks the peripheral β-adrenergic receptor sites, such as those in the lung, as well as the β-adrenergic receptor sites in the heart. Propranolol is contraindicated in patients who suffer from asthma or chronic obstructive lung disease, because following its administration to such patients, an increase in airway resistance and bronchial constriction has been observed. Accordingly, I have now discovered potent cardiac selective β-adrenergic blocking agents which are effective for the treatment or palliation of cardiac arrythmias, and which further can safely be used by patients suffering from asthma or chronic obstructive lung disease. The compounds are further effective for the treatment or palliation of angina pectoris and again can be safely applied to patients who also suffer from asthma or chronic lung disease.

SUMMARY OF THE INVENTION

In summary the compounds of the invention can be represented by the following generic formula:

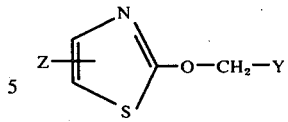

wherein Z is at either the 4- or 5-position of the thiazole ring and has the formula:

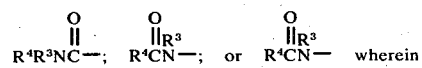

wherein $R^3$ and $R^4$ are independently selected from the group of hydrogen, alkyl, cycloalkyl, aryl, arylalkyl, terminally substituted alkyl, and groups having the formulas —$(CH_2)_{n+1}NR^8R^9$ or —$(CH_2)_nR^{10}$ wherein n is a whole integer of from one through four, $R^8$ and $R^9$ are independently hydrogen and alkyl groups having one through four carbon atoms, and $R^{10}$ is cycloalkyl having from three through eight carbon atoms; and whrein when Z is the group

then $R^4$ cannot be hydrogen;

Y is selected from the group having the formulas:

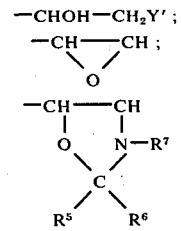

wherein Y' is amino or amino derivative or nitrogen heterocycle; $R^7$ is hydrogen, lower alkyl, aryl or arylalkyl; $R^5$ and $R^6$ are independently selected from the group of hydrogen, lower alkyl, phenyl, arylalkyl or together with the carbon atom to which they are joined form a cycloalkyl having from five through seven carbon atoms.

Also encompassed within the invention are pharmaceutical acceptable salts of the above compounds.

In summary the process of the invention for preparing the compounds, of the invention, wherein Y is

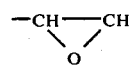

comprises treating the corresponding 3-(4- or 5-Z-thiazol-2-oxy)-1-alkylsulfonyl or phenylsulfonyl-2-propanol derivative at the 2,3-position with a strong base.

In summary the process of the invention for preparing the compounds, of the invention, wherein Y is the group —CHOH-CH$_2$-Y' comprises treating the compounds of the invention wherein Y is

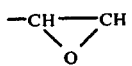

with ammonia or amine having the desired R¹ and R² substituent. Alternatively these compounds can be prepared, according to the invention, by hydrolysis of the corresponding Y is oxazolidine compounds of the inventon.

In summary the process of the invention of preparing the compounds of the invention wherein Y is an oxazolidine group, in the Z is

series, comprises condensation of a 2-bromo or 2-chloro-thiazole having the desired 4- or 5-position substituent with a 5-hydroxymethyl-oxazolidine having the desired $R^5$, $R^6$ and $R^7$ -substituents. All of the oxazolidine compounds can be prepared by treating the corresponding compounds of the invention where Y is an amino-propanol derivative with the desired $R^5$, $R^6$ aldehyde or ketone.

In summary the pharmaceutical compositions of the invention include both solutions and solids or powders comprising one or more of the compounds, of the inventiion, wherein Y is an amino propanol type derivative and/or one or more compounds of the invention, wherein Y is an oxazolidine derivative in combination with a suitable pharmaceutical solution (e.g. sterile water) or pharmaceutical solid excipients.

The invention will be further described herein below.

DESCRIPTION OF THE INVENTION AND PREFERRED EMBODIMENTS

The compounds of the invention can be represented by the following sub-generic formulas:

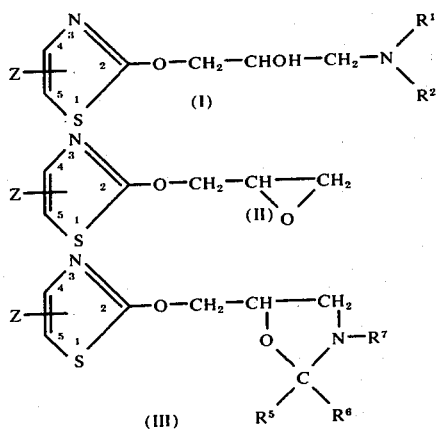

wherein $R^1$ and $R^2$ are independently selected from the group of hydrogen, lower alkyl, cycloalkyl having from three through seven ring atoms, lower alkenyl, phenyl, lower phenylalkyl, substituted phenyl, substituted lower phenylalkyl, hydroxy lower alkyl, (lower alkoxy) lower alkyl, lower alkyl (N-heterocyclic having from five through seven ring atoms including one or two heteroatoms selected from the group of nitrogen, oxy-gen and sulfur and wherein at least one of said heteroatoms is nitrogen) and groups having the formulas

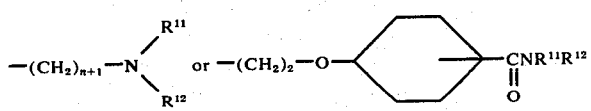

wherein n is a whole integer of from one through four; and $R^{11}$ and $R^{12}$ are independently hydrogen or lower alkyl; or $R^1$ and $R^2$ together with the nitrogen atom to which they are joined form a nitrogen heterocycle having from five through seven ring atoms having one or two heteroatoms selected from the group consisting of nitrogen, oxygen and sulfur and wherein at least one of said heteroatoms is nitrogen or $R^1$ and $R^2$ form a substitute nitrogen heterocycle having from five through seven ring atoms including one or two heteroatoms selected from the group of nitrogen, oxygen and sulfur and wherein at least one of said heteroatoms is nitrogen and having one or two substituents independently selected from the group of lower alkyl, and hydroxy(-lower alkyl);

Z is a substituent on the thiazole ring at either the 4- or 5-position selected from the group having the formulas:

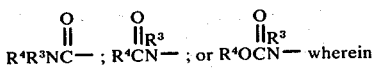

wherein $R^3$ and $R^4$ are independently selected from the group of hydrogen; alkyl having from one through 12 carbon atoms; cycloalkyl having from three through 12 carbon atoms; phenyl; lower phenylalkyl, substituted phenyl, substituted lower phenylalkyl; terminally substituted alkyl group having from two through 12 carbon atoms having one substituted terminal carbon atom having from one through three substituents independently selected from the group of hydroxy, acyloxy having from two through 12 carbon atoms and alkoxy having from one through six carbon atoms; and groups having the formulas $-(CH_2)_{n+1}NR^8R^9$ or $-(CH_2)_nR^{10}$ wherein n is a whole integer of from one through four, $R^8$ and $R^9$ are independently selected from the group of hydrogen and alkyl groups having from one through four carbon atoms and $R^{10}$ is cycloalkyl having from three through eight carbon atoms; and wherein when Z is the group

then $R^4$ cannot be hydrogen;

$R^5$ and $R^6$ are independently selected from the group of hydrogen, lower alkyl, phenyl, lower phenylalkyl, substituted lower phenylalkyl or together with the carbon atom to which they are joined form a cycloalkyl having from five through seven carbon atoms;

$R^7$ is hydrogen, lower alkyl, aryl or arylalkyl.

Also encompassed within the invention are pharmaceutically acceptable salts of the above compound of formulas I and III.

The compounds of the invention have an asymmetric carbon aton in the propane side chain and thus exist as optical isomers. Correspondingly the above formulas are intended to represent the respective individual (+) and (−) optical isomers as well as mixtures of such isomers and the individual isomers as well as mixtures thereof are encompassed within the invention. Where the compounds of the invention have 1-positioned substituents, on the propane chain, which have asymmetric atoms, the compounds exhibit further optical acitivty with respect to such asymmetric atoms.

DEFINITIONS

As used herein above and below, the following terms shall have the following meaning unless expressly stated to the contrary. The term alkyl, or alkylene, refers to both straight and branched chain alkyl groups. Where primed numerals are used with respect to alkyl groups, branched alkyl groups are meant with the primed numerals designating the position of lesser alkyl groups on the longer primary alkyl chain. Thus, for example, the term 5'-methylhexyl refers to the group

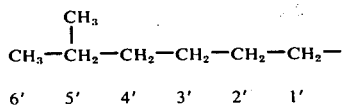

The term lower alkyl refers to both straight and branched chain alkyl groups having a total of from one through six carbon atoms and thus includes primary, secondary, and tertiary alkyl groups. Typical lower alkyls include, for example, methyl, ethyl, n-propyl, isopropyl, n-butyl, t-butyl, n-hexyl and the like. The term cycloalkyl refers to cyclic hydrocarbon groups having from three through 12 carbon atoms and preferably three through seven carbon atoms such as, for example, cyclopropyl, cyclopentyl, cycloheptyl and the like. The term alkenyl refers to monoethylenically unsaturated aliphatic groups and the term lower alkenyl refers to such groups having from two through six carbon atoms and wherein the double bond can be between any two adjacent carbon atoms. Typical lower alkenyl groups include, for example, vinyl, propenyl, and the like. The term alkoxy refers to groups having the formula R'O wherein R' is alkyl and correspondingly the term lower alkoxy refers to the group having the formula R'O- wherein R' is lower alkyl. Typical alkoxy groups include, for example, methoxy, ethoxy, t-butoxy and the like. The term (lower alkoxy) lower alkyl or perhaps more correctly (lower alkoxy) lower alkylene refers to the group —R'-OR'' wherein R' is lower alkylene and OR'' is lower alkoxy. The term hydroxy lower alkyl or hydroxy lower alkylene refers to groups having the formula HOR'- wherein R' is lower alkylene. Typical hydroxyalkyl or hydroxyalkylene groups include, for example, α-hydroxyethylene, β-hydroxypropylene, hydroxyisopropylene and the like. The term terminally substituted alkyl (or alkylene) refers to alkylene groups having from two through 12 carbon atoms in which the terminal carbon atom, or in the case of groups, such as t-butyl, which have more than one terminal carbon, wherein one of such terminal carbon atoms are substituted with from one through three substituents independently selected from the group of hydroxy, acyloxy and alkoxy. Typical terminally substituted alkyl groups include 2-hydroxy-ethylene, 3-acetoxypropyl, β-methoxyethylene and the like. The term carboxy refers to the group —COOH. The term halo refers to iodo, bromo, chloro and fluoro groups. The term acyl refers to acyl groups derived from carboxylic acids having from two through 12 carbon atoms such as acetyl, propionyl, butyryl, valeryl, isovaleryl, hexanoyl, heptanoyl, octanoyl, nonoanoyl, undecanoyl, lauroyl, benzoyl, phenylacetyl, phenlpropionyl, o-, m-, p-toluoyl, β-cyclopentylpropionyl, formyl and the like.

The term alkoxycarbonyl refers to groups having the formula

wherein $R'_3$ is an alkyl group having from one through 11 carbon atoms. Typical alkoxycarbonyl groups thus include, for example, methoxycarbonyl, propoxycarbonyl, isopropoxycarbonyl, undecanoxycarbonyl and the like. The term acyloxy refers to groups derived from carboxylic acids having from two through 12 carbon atoms such as acetyloxy, propionyloxy, butyryloxy, valeryloxy, isovaleryloxy, hexanoyloxy, heptanoyloxy, octanoyloxy, nonanoyloxy, undecanoyloxy, lauroyloxy, benzoyloxy, phenylacetyloxy, phenylpropionyloxy, o—, m—, p-toluoyloxy, β-cyclopentylpropionyloxy and the like.

The term aryl refers to phenyl or substituted phenyls as defined herein below. By the term alkylaryl is meant an alkyl substituted phenyl group having one or more alkyl substituents and having up to 12 carbon atoms such as o-tolyl, m-tolyl, p-isopropylphenyl, 2,3-dimethylphenyl, 3,5-dimethylphenyl and the like. The term lower phenylalkyl refers to an alkyl group having from one through six carbon atoms and having a phenyl substituent. The term substituted lower phenylalkyl refers to an alkyl group having one through six carbon atoms and having a substituted phenyl (as defined herein) substituent. The term arylalkyl refers to the group of lower phenylalkyl and substituted lower phenylalkyl inclusive. The term substituted phenyl refers to phenyl groups which have one or more substituents independently selected from the group of hydroxy, lower alkyl, lower alkoxy and halo groups. Typical substituted phenyl groups include, for example, p-hydroxyphenyl, p-ethylphenyl, p-t-butoxyphenyl, p-fluorophenyl, p-chlorophenyl and the corresponding ortho and meta isomers, 3,4-dimethoxyphenyl, 3-bromo-4-chlorophenyl and the like.

The term alkylamino refers to the group having the formula R'HN wherein R' is alkyl and the term lower alkylamino refers to such groups wherein R' is lower alkyl. The term dialkylamino refers to the group having the formula $R'_1R'_2N$- wherein $R'_1$ and $R'_2$ are independently alkyl. Typical lower dialkylamino groups include, for example, dimethylamino, N-methyl-N-ethylamino, diethylamino, N-t-butyl-N-isopropylamino and the like.

The term aminocarbonyl or carbamoyl refers to the group having the formula

The term substituted aminocarbonyl (e.g. alkylaminocarbonyl) or substituted carbamoyl refers to the group having the formula

wherein $R^3$ is as defined herein. Typical alkylaminocarbonyl or alkylcarbamoyl groups include, for example, methylaminocarbonyl or methylcarbamoyl; heptylaminocarbonyl or heptylcarbamoyl; n-nonylaminocarbonyl or n-nonylcarbamoyl; and the like. The term disubstituted aminocarbonyl or disubstituted carbamoyl refers to groups having the formula

wherein $R^3$ and $R^4$ are as defined herein. Typical dialkylaminocarbonyl or dialkylcarbamoyl groups include, for example, N-methyl-N-heptylaminocarbonyl or N-methyl-N-heptylcarbamoyl; diheptylaminocarbonyl or diheptylcarbamoyl, N-(n-nonyl)-N-(n-ocytyl)-aminocarbonyl or N-(n-nonyl)-N-(n-ocytyl)-aminocarbamoyl and the like. The term hydroxyalkylaminocarbonyl or hydroxyalkylenaminocarbonyl or hydroxyalkylcarbamoyl refers to groups having the formula

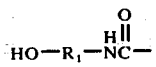

wherein $R_1$ is an alkylene group having from two through twelve carbon atoms. The term alkoxyalkylaminocarbonyl or alkoxyalkylenaminocarbonyl or alkoxyalkylcarbamoyl refers to groups having the formula

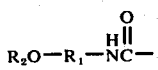

wherein $R_1$ is as defined immediately above and $R_2$ is alkyl. The term acyloxyalkylaminocarbonyl or acyloxyalkylcarbamoyl refers to groups having the formula

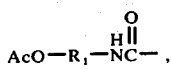

wherein $R_1$ is as defined above and AcO is acyloxy as defined herein above.

The term formamido refers to the group having the formula

The term N-substituted formamido (e.g. N-alkylformamido) refers to the groups having the formula

wherein $R^3$ is as defined herein. The term substituted amido (e.g. alkylamido) or substituted carbonylamino e.g. alkylcarbonylamino) or acylamino refer to the group having the formula

wherein $R^4$ is as defined herein. The term N-(substituted)-substituted amido or N-(substituted)-substituted carbonylamino or N-substituted-acylamino refer to groups having the formula

wherein $R^3$ and $R^4$ is as defined herein above. Typical groups having the formula

include, for example, N-heptyl-acetamido or N-heptyl acetylamino; or N-heptyl-methylcarbonylamino; N-methyl-heptylcarbonylamino, and the like.

The term substituted-oxy carbonylamino (e.g. alkoxycarbonylamino; phenoxycarbonylamino refers to the group having the formula

wherein $R^4$ is as defined herein. The term N-substituted-substituted-oxy carbonylamino (e.g. N-alkyl-alkoxycarbonylamino; N-alkylphenoxycarbonylamino refers to groups having the formulas

wherein $R^3$ and $R^4$ are as defined herein. Typical

groups include, for example, N-methyl-heptoxycarbonylamino, N-heptyl-t-butoxycarbonylamino and the like.

The terms N-heterocycle or nitrogenheterocycle refer to both saturated and unsaturated heterocyclics having from five through seven ring atoms, one of which is nitrogen and which can optionally also contain a second heterocycle ring atom selected from the group of nitrogen, sulfur and oxygen. Also encompassed within the term are substituted N-heterocyclics having one or two substituents independently selected from the group of lower alkyl, hydroxylower alkyl, and halo. Typical N-heterocycles include, for example, those having the formulas:

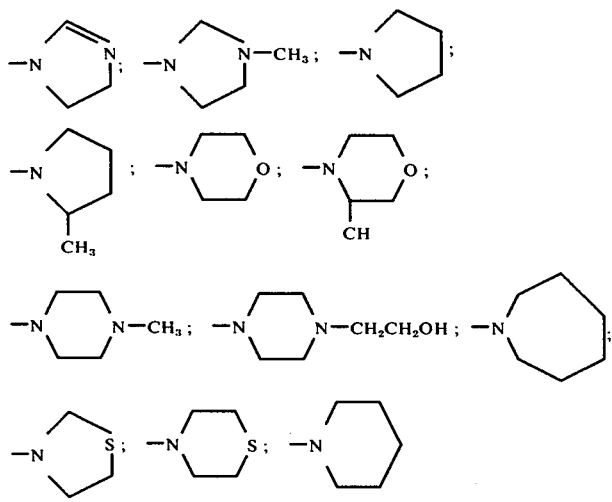

and the like.

The term N-heterocycle alkyl or N-heterocycle alkylene refers to a lower alkylene group having an N-heterocyclic substituent as defined herein above. Such groups can be represented by the formula XR'- wherein X is N-heterocyclic and R' is lower alkylene. With respect to the compounds of the invention, the morpholino, pyrrolidinyl, piperidino, piperazinyl and the group

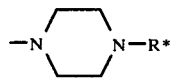

wherein R* is lower alkyl or lower hydroxyalkyl are the preferred heterocyclic groups.

The term pharmaceutically acceptable salts refers to pharmacetuically acceptable hydrogen-anion addition salts which do not adversely affect the pharmaceutical properties of the parent compounds. With respect to the addition salts, suitable inorganic anions include, for example, chloride, bromide, iodide, sulfuate, phosphate, carbonate, nitrate, hydrocarbonate, sulfate, and the like. Suitable organic anions include, for example, acetate, benzoate, lactate, pierato, propionate, butyrate, valerate, tartrate, maleate, fumarate, citrate, succinate, tosylate, ascorbate, pamoate, nicotinate, adipate, glyconate and the like.

Typical illustrations of the compounds of formula I can be had, for example, herein below by reference to Examples 4–7, 9, 11, 12, 15–18. The preferred $R^1$ and $R^2$ substituents are those wherein one of $R^1$ or $R^2$ is hydrogen and the other is selected from the group of isopropyl; secbutyl; t-butyl; cyclopropyl; cyclopentyl; α-phenylethyl; β-hydroxyethyl; α-phenylpropyl; β-(3,4-dimethoxyphenyl)-ethyl); β-(4-hydroxyphenyl)-ethyl; α-methyl-β-(4-hydroxyphenyl)-ethyl; γ-(4-hydroxyphenyl)-propyl; α-methyl-γ-(4-hydroxyphenyl)-propyl; α-methyl-γ-phenylpropyl; and β-(4-aminocarbonylphenoxy)-ethyl. The preferred $R^3$ and $R^4$ substituent compounds of formula I are those wherein $R^3$ is hydrogen and $R^4$ is selected from the group of n-pentyl, n-hexyl, 3'-methylhexyl, 1'-methylhexyl, 4'-ethylhexyl, 3'-propylhexyl, n-heptyl; n-ocytl, cycloheptyl, cyclohexyl, β-cyclopentylethyl, γ-cyclopentylpropyl, 4'-cyclopentylbutyl, γ-cyclohexylpropyl, benzyl, β-methoxyethyl, and γ-dimethylaminopropyl and especially 5'-methylhexyl and 4'-methylhexyl. The particularly preferred compounds of formula I are:

1-t-butylamino-3-(5-3'-methylhexylaminocarbonylthiazol-2-oxy)-2-propanol;

1-isopropylamino-3-(5-3'-methylhexylaminocarbonylthiazol-2-oxy)-2-propanol;

1-[β-(4-aminocarbonylphenoxy)-ethylamino]-3-(5-3'-methylhexylaminocarbonylthiazol-2-oxy)-2-propanol;

1-t-butylamino-3-(5-4'-methylhexylaminocarbonylthiazol-2-oxy)-2-propanol;

1-isopropylamino-3-(5-4'-methylhexylaminocarbonylthiazol-2-oxy)-2-propanol;

1-[β-(4-aminocarbonylphenoxy)-ethylamino]-3-(5-4'-methylhexylaminocarbonylthiazol-2-oxy)-2-propanol;

1-t-butylamino-3-(5-5'-methylhexylaminocarbonylthiazol-2-oxy)-2-propanol;

1-isopropylamino-3-(5-5'-methylhexylaminocarbonylthiazol-2-oxy)-2-propanol;

1-[β-(4-aminocarbonylphenoxy)-ethylamino]-3-(5-5'-methylhexylaminocarbonylthiazol-2-oxy)-2-propanol;

1-t-butylamino-3-(5-4'-ethylhexylaminocarbonylthiazol-2-oxy)-2-propanol;

1-isopropylamino-3-(5-4'-ethylhexylaminocarbonylthiazol-2-oxy)-2-propanol;

1-[β-(4-aminocarbonylphenoxy)-ethylamino]-3-(5-4'-ethylhexylaminocarbonylthiazol-2-oxy)-2-propanol;

1-t-butylamino-3-(5-3'-propylhexylaminocarbonylthiazol-2-oxy)-2-propanol;

1-isopropylamino-3-(5-3'-propylhexylaminocarbonylthiazol-2-oxy)-2-propanol;

1-[β-(4-aminocarbonylphenoxy)-ethylamino]-3-(5-3'-propylhexylaminocarbonylthiazol-2-oxy)-2-propanol;

1-t-butylamino-3-(5-n-heptylaminocarbonylthiazol-2-oxy)-2-propanol;

1-isopropylamino-3-(5-n-heptylaminocarbonylthiazol-2-oxy)-2-propanol;

1-[β-(4-aminocarbonylphenoxy)-ethylamino]-3-(5-n-heptylaminocarbonylthiazol-2-oxy)-2-propanol;

1-t-butylamino-3-(5-n-hexylaminocarbonylthiazol-2-oxy)-2-propanol;

1-isopropylamino-3-(5-n-hexylaminocarbonylthiazol-2-oxy)-2-propanol;

1-[β-(4-aminocarbonylphenoxy)-ethylamino]-3-(5-n-hexylaminocarbonylthiazol-2-oxy)-2-propanol;

1-t-butylamino-3-(5-β-cyclopentylethylaminocarbonylthiazol-2-oxy)-2-propanol;

1-isopropylamino-3-(5-β-cyclopentylethylaminocarbonylthiazol-2-oxy)-2-propanol;

1-[β-(4-aminocarbonylphenoxy)-ethylaminol]-3-(5-β-cyclopentylethylaminocarbonylthiazol-2-oxy)-2-propanol;

1-t-butylamino-3-(5-γ-cyclopentylpropylaminocarbonylthiazol-2-oxy)-2-propanol;

1-isopropylamino-3-(5-γ-cyclopentylpropylaminocarbonylthiazol-2-oxy)-2-propanol;

1-[β-(4-aminocarbonylphenoxy)-ethylamino]-3-(5-γ-cyclopentylpropylaminocarbonylthiazol-2-oxy)-2-propanol;

1-t-butylamino-3-(5-4'-cyclopentylbutylaminocarbonylthiazol-2-oxy)-2-propanol;

1-isopropylamino-3-(5-4'-cyclopentylbutylaminocarbonylthiazol-2-oxy)-2-propanol;

1-[β-(4-aminocarbonylphenoxy)-ethylamino]-3-(5-4'-cyclopentylbutylaminocarbonylthiazol-2-oxy)-2-propanol;

1-t-butylamino-3-(5-γ-cyclohexylpropylaminocarbonylthiazol-2-oxy)-2-propanol;

1-isopropylamino-3-(5-γ-cyclohexylpropylaminocarbonylthiazol-2-oxy)-2-propanol;

1-[β-(4-aminocarbonylphenoxy)-ethylamino]-3-(5-γ-cyclohexylpropylaminocarbonylthiazol-2-oxy)-2-propanol;

1-t-butylamino-3-(5-3'-methylhexylcarbonylaminothiazol-2-oxy)-2-propanol;

1-isopropylamino-3-(5-3'-methylhexylcarbonylaminothiazol-2-oxy)-2-propanol;

1-[β-(4-aminocarbonylphenoxy)-ethylamino]-3-(5-3'-methylhexylcarbonylaminothiazol-2-oxy)-2-propanol;

1-t-butylamino-3-(5-4'-methylhexylcarbonylaminothiazol-2-oxy)-2-propanol;

1-isopropylamino-3-(5-4'-methylhexylcarbonylaminothiazol-2-oxy)-2-propanol;

1-[β-(4-aminocarbonylphenoxy)-ethylamino]-3-(5-4'-methylhexylcarbonylaminothiazol-2-oxy)-2-propanol;

1-t-butylamino-3-(5-5'-methylhexylcarbonylaminothiazol-2-oxy)-2-propanol;

1-isopropylamino-3-(5-5'-methylhexylcarbonylaminothiazol-2-oxy)-2-propanol;

1-[β-(4-aminocarbonylphenoxy)-ethylamino]-3-(5-5'-methylhexylcarbonylaminothiazol-2-oxy)-2-propanol;

1-t-butylamino-3-(5-4'-ethylhexylcarbonylaminothiazol-2-oxy)-2-propanol;

1-isopropylamino-3-(5-4'-ethylhexylcarbonylaminothiazol-2-oxy)-2-propanol;

1-[β-(4-aminocarbonylphenoxy)-ethylamino]-3-(5-4'-ethylhexylcarbonylaminothiazol-2-oxy)-2-propanol;

1-t-butylamino-3-(5-3'-propylhexylcarbonylaminothiazol-2-oxy)-2-propanol;

1-isopropylamino-3-(5-3'-propylhexylcarbonylaminothiazol-2-oxy)-2-propanol;

1-[β-(4-aminocarbonylphenoxy)-ethylamino]-3-(5-3'-propylhexylcarbonylaminothiazol-2-oxy)-2-propanol;

1-t-butylamino-3-(5-n-heptylcarbonylaminothiazol-2-oxy)-2-propanol;

1-isopropylamino-3-(5-n-heptylcarbonylaminothiazol-2-oxy)-2-propanol;

1-[β-(4-aminocarbonylphenoxy)-ethylamino]-3-(5-n-heptylcarbonylaminothiazol-2-oxy)-2-propanol;

1-t-butylamino-3-(5-n-hexylcarbonylaminothiazol-2-oxy)-2-propanol;

1-isopropylamino-3-(5-n-hexylcarbonylaminothiazol-2-oxy)-2-propanol;

1-[β-(4-aminocarbonylphenoxy-ethylamino]-3-(5-n-hexylcarbonylaminothiazol-2-oxy)-2-propanol;

1-t-butylamino-3-(5-β-cyclopentylethylcarbonylaminothiazol-2-oxy)-2-propanol;

1-isopropylamino-3-(5-β-cyclopentylethylcarbonylaminothiazol-2-oxy)-2-propanol;

1-[β-(4-aminocarbonylphenoxy)-ethylamino]-3-(5-β-cyclopentylethylcarbonylaminothiazol-2-propanol;

1-t-butylamino-3-(5-γ-cyclopentylpropylcarbonylaminothiazol-2-oxy)-2-propanol;

1-isopropylamino-3-(5-γ-cyclopentylpropylcarbonylaminothiazol-2-oxy)-2-propanol;

1-[β-(4-aminocarbonylphenoxy)-ethylamino]-3-(5-γ-cyclopentylpropylcarbonylaminothiazol-2-oxy)-2-propanol;

1-t-butylamino-3-(5-4'-cyclopentylbutylcarbonylaminothiazol-2-oxy)-2-propanol;

1-isopropylamino-3-(5-4'-cyclopentylbutylcarbonylaminothiazol-2-oxy)-2-propanol;

1-[β-(4-aminocarbonylphenoxy)-ethylamino]-3-(5-4'-cyclopentylbutylcarbonylaminothiazol-2-oxy)-2-propanol;

1-t-butylamino-3-(5-γ-cyclohexylpropylcarbonylaminothiazol-2-oxy)-2-propanol;

1-isopropylamino-3-(5-γcyclohexylpropylcarbonylaminothiazol-2-oxy)-2-propanol;

1-[β-(4-aminocarbonylphenoxy)-ethylamino]-3-(5-γ-cyclohexylpropylcarbonylaminothiazol-2-oxy)-2-propanol;

1-t-butylamino-3-(5-3'-methylhexoxycarbonylaminothiazol-2-oxy)-2-propanol;

1-isopropylamino-3-(5-3'-methylhexoxycarbonylaminothiazol-2-oxy)-2-propanol;

1-[β-(4-aminocarbonylphenoxy)-ethylamino]-3-(5-3'-methylhexoxycarbonylaminothiazol-2-oxy)-2-propanol;

1-t-butylamino-3-(5-4'-methylhexoxycarbonylaminothiazol-2-oxy)-2-propanol;

1-isopropylamino-3-(5-4'-methylhexoxycarbonylaminothiazol-2-oxy)-2-propanol;

1-[β-(4-aminocarbonylphenoxy)-ethylamino]-3-(5-4'-methylhexoxycarbonylaminothiazol-2-oxy)-2-propanol;

1-t-butylamino-3-(5-5'-methylhexoxycarbonylaminothiazol-2-oxy)-2-propanol;

1-isopropylamino-3-(5-5'-methylhexoxycarbonylaminothiazol-2-oxy)-2-propanol;

1-[β-(4-aminocarbonylphenoxy)-ethylamino]-3-(5-5'-methylhexoxycarbonylaminothiazol-2-oxy)-2-propanol;

1-t-butylamino-3-(5-4'-ethylhexoxycarbonylaminothiazol-2-oxy)-2-propanol;

1-isopropylamino-3-(5-4'-ethylhexoxycarbonylaminothiazol-2-oxy)-2-propanol;

1-[β-(4-aminocarbonylphenoxy)-ethylamino]-3-(5-4'-ethylhexoxycarbonylaminothiazol-2-oxy)-2-propanol;

1-t-butylamino-3-(5-3'-propylhexoxycarbonylaminothiazol-2-oxy)-2-propanol;

1-isopropylamino-3-(5-3'-propylhexoxycarbonylaminothiazol-2-oxy)-2-propanol;

1-[β-(4-aminocarbonylphenoxy)-ethylamino]-3-(5-3'-propylhexoxycarbonylaminothiazol-2-oxy)-2-propanol;

1-t-butylamino-3-(5-n-heptoxycarbonylaminothiazol-2-oxy)-2-propanol;

1-isopropylamino-3-(5-n-heptoxycarbonylaminothiazol-2-oxy)-2-propanol;

1-[β-(4-aminocarbonylphenoxy)-ethylamino]-3-(5-n-heptoxycarbonylaminothiazol-2-oxy)-2-propanol;

1-t-butylamino-3-(5-n-hexoxycarbonylaminothiazol-2-oxy)-2-propanol;

1-isopropylamino-3-(5-n-hexoxycarbonylaminothiazol-2-oxy)-2-propanol;

1-[β-(4-aminocarbonylphenoxy)-ethylamino]-3-(5-n-hexoxycarbonylaminothiazol-2-oxy)-2-propanol;

1-t-butylamino-3-(5-β-cyclopentylethoxycarbonylaminothiazol-2-oxy)-2-propanol;

1-isopropylamino-3-(5-β-cyclopentylethoxycarbonylaminothiazol-2-oxy)-2-propanol;

1-[β-(4-aminocarbonylphenoxy)-ethylamino]-3-(5-β-cyclopentylethoxycarbonylaminothiazol-2-oxy)-2-propanol;

1-t-butylamino-3-(5-γ-cyclopentylpropoxycarbonylaminothiazol-2-oxy)-2-propanol;

1-isopropylamino-3-(5-γ-cyclopentylpropoxycarbonylaminothiazol-2-oxy)-2-propanol;

1-[β-(4-aminocarbonylphenoxy)-ethylamino]-3-(5-γ-cyclopentylpropoxycarbonylaminothiazol-2-oxy)-2-propanol;

1-t-butylamino-3-(5-4'-cyclopentylbutoxycarbonylaminothiazol-2-oxy)-2-propanol;

1-isopropylamino-3-(5-4'-cyclopentylbutoxycarbonylaminothiazol-2-oxy)-2-propanol;

1-[β-(4-aminocarbonylphenoxy)-ethylamino]-3-(5-4'-cyclopentylbutoxycarbonylaminothiazol-2-oxy)-2-propanol;

1-t-butylamino-3-(5-γ-cyclohexylpropoxycarbonylaminothiazol-2-oxy)-2-propanol;

1-isopropylamino-3-(5-γ-cyclohexylpropoxycarbonylaminothiazol-2-oxy)-2-propanol; and 1-[β-(4-aminocarbonylphenoxy)-ethylamino]-3-(5-γ-cyclohexylpropoxycarbonylaminothiazol-2-oxy)-2-propanol.

Typical illustrations of the compounds of formula II can be had, for example, herein below by reference to Example 3. Further since the primary use of compounds of formula II is as intermediates for the compounds of formula I, the preferred $R^3$ and $R^4$ substituents are the same as listed above for formula I and the particularly preferred compounds of formula II are the precursors corresponding to the particularly preferred compounds of formula I as set forth herein above.

Typical illustrations of the compounds of formula III can be had, herein below, by reference to Examples 10 and 13–18. The preferred $R^3$ and $R^4$ substituents for the compounds of formula III are the same as listed above for the compounds as formula I. The simpler $R^5$ and $R^6$ substituents are preferred (i.e. $R^5$ and $R^6$ are other than substituted phenyl) and the preferred compounds of formula III are those wherein $R^5$ and $R^6$ are each hydrogen or each methyl. The preferred $R^7$ substituents are methyl, isopropyl, sec-butyl, t-butyl, cyclopropyl, cyclopentyl, α-phenylethyl, γ-phenylpropyl, β-(3,4-dimethoxyphenyl)-ethyl, β-(4-hydroxyphenyl)-ethyl, α-methyl-β-(4-hydroxyphenyl)-ethyl, γ-(4-hydroxyphenyl)-butyl, α-methyl-γ-(β-hydroxyphenyl)-propyl, and α-methyl-γ-phenylpropyl. The particularly preferred compounds of formula III are:

5-(5-3'-methylhexylaminocarbonylthiazol-2-oxy)-methylene-N-t-butyloxazolidine;

5-(5-3'-methylhexylaminocarbonylthiazol-2-oxy)-methylene-N-isopropyloxazolidine;

5-(5-4'-methylhexylaminocarbonylthiazol-2-oxy)-methylene-N-t-butyloxazolidine;

5-(5-4'-methylhexylaminocarbonylthiazol-2-oxy)-methylene-N-isopropyloxazolidine;

5-(5-5'-methylhexylaminocarbonylthiazol-2-oxy)-methylene-N-t-butyloxazolidine;

5-(5-5'-methylhexylaminocarbonylthiazol-2-oxy)-methylene-N-isopropyloxazolidine;

5-(5-4'-ethylhexylaminocarbonylthiazol-2-oxy)-methylene-N-t-butyloxazolidine;

5-(5-4'-ethylhexylaminocarbonylthiazol-2-oxy)-methylene-N-isopropyloxazolidine;

5-(5-3'-propylhexylaminocarbonylthiazol-2-oxy)-methylene-N-t-butyloxazolidine;

5-(5-3'-propylhexylaminocarbonylthiazol-2-oxy)-methylene-N-isopropyloxazolidine;

5-(5-n-heptylaminocarbonylthiazol-2-oxy)-methylene-N-t-butyloxazolidine;

5-(5-n-heptylaminocarbonylthiazol-2-oxy)-methylene-N-isopropyloxazolidine;

5-(5-β-cyclopentylethylaminocarbonylthiazol-2-oxy)-methylene-N-t-butyloxazolidine;

5-(5-β-cyclopentylethylaminocarbonylthiazol-2-oxy)-methylene-N-isopropyloxazolidine;

5-(5-γ-cyclopentylpropylaminocarbonylthiazol)-2-oxy)-methylene-N-t-butyloxazolidine;

5-(5-γ-cyclopentylpropylaminocarbonylthiazol-2-oxy)-methylene-N-isopropyloxazolidine;

5-(5-4'-cyclopentylbutylaminocarbonylthiazol-2-oxy)-methylene-N-t-butyloxazolidine;

5-(5-4'-cyclopentylbutylaminocarbonylthiazol-2-oxy)-methylene-N-isopropyloxazolidine;

5-(5-γ-cyclohexylpropylaminocarbonylthiazol-2-oxy)-methylene-N-t-butyloxazolidine;

5-(5-γ-cyclohexylpropylaminocarbonylthiazol-2-oxy)-methylene-N-isopropyloxazolidine; and 5-(5-3'-methylhexylcarbonylaminothiazol-2-oxy)-methylene-N-t-butyloxazolidine.

The corresponding 4'-position substituted thiazole position isomer corresponding to the particularly preferred 5-position compounds enumerated above with respect to formulas I, II and III, are also preferred but generally the 5-position isomers have superior properties to the 4-position isomers.

The preferred pharmaceutically acceptable salts are hydrogen addition salts of chloride, bromide, sulfate, maleate, lactate, tartrate, succinate and especially chloride. Thus, the preferred salts are the preferred anion addition salts of formulas I and III and correspondingly the particularly preferred salts are the preferred hydrogen anion addition salts of the preferred and particularly preferred compounds of formulas I and III and especially the hydrochloride salts.

The compounds of the invention can be conveniently prepared by the following process, which can be represented by the following schematic overall reaction equation sequence:

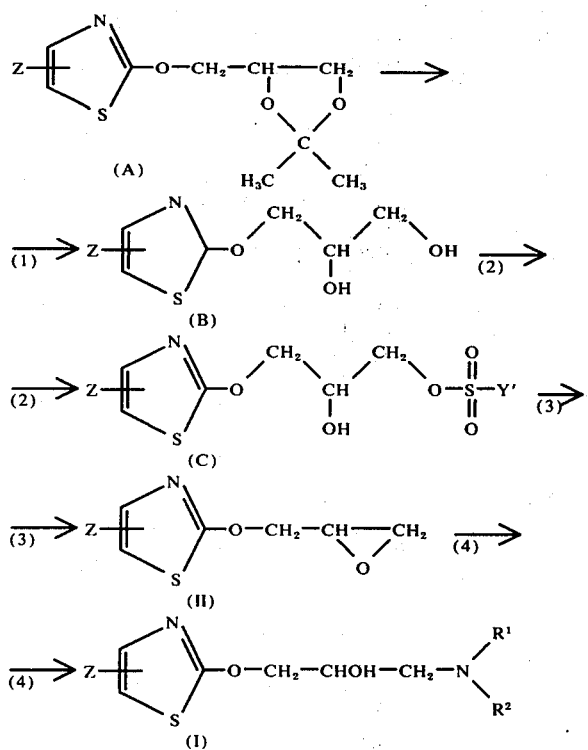

wherein Y' is alkyl or phenyl, and R$^1$, R$^2$ and Z have the same meanings as set forth herein above.

Step 1 can be conveniently effected by treating the compound of formula A with a suitable organic or inorganic acid, preferably in a suitable inert solvent. Typically this treatment is conducted at temperatures in the range of about from 0° to 65° C and preferably about 25°–30° C, for about from 3 minutes to 18 hours and preferably about from one to four hours. However, temperatures, reaction times and mole ratios both above and below these ranges can also be used. Suitable inorganic acids which can be used include, for example, hydrochloric acid, hydrobromic acid, sulfuric acid, phosphoric acid and the like. Suitable organic acids which can be used include, for example, formic acid, oxalic acid, acetic acid, propionic acid, and the like. Suitable solvents which can be used include, for example, water, methanol, acetone, monoglyme, ether and the like. Good results are typically obtained by using aqueous formic acid solution.

Step 2 of the above process can be effected by treating the compound of formula B with a suitable phenyl sulfonyl chloride or bromide or alkyl sulfonyl chloride or bromide, in a suitable inert organic solvent in the presence of a base. The particular sulfonyl derivative used in largely immaterial since the sulfonyl substituent is split off during the next step. Thus, typically other phenyl sulfonyl chloride or bromide or alkyl sulfonyl chloride or bromide derivatives can also be used. Typically this treatment is conducted at temperatures in the range of about from 0° to 60° C and preferably about from 0° to 25° C for about from five minutes to 18 hours, preferably about from 10 minutes to 45 minutes, using mole ratios in the range of about from 1.0 to 1.1 moles of sulfonyl derivatives per mole of compound of formula C. However, temperatures, treatment times, and mole ratios both above and below these ranges can also be used. Suitable phenyl sulfonyl chlorides or bromides, which can be used include, for example, benzene sulfonyl chloride, benzene sulfonyl bromide, or p-toluene sulfonyl chloride, p-ethyl benzene sulfonyl bromide, and the like. Suitable alkyl sulfonyl chlorides, and bromides, which can be used include, for example, methane sulfonyl chloride, methane sulfonyl bromide and the like. Suitable organic bases which can be used include, for example, pyridine, triethylamine or tertiary amines, and the like. Suitable solvents include methyl dichloride, diethyl ether, tetrahydrofuran and the like. Pyridine can be conveniently used as both the base and the solvent.

Step 3 can be conveniently effected by treating the compound of formula C with a strong base preferably in an inert organic solvent. Conveniently this treatment is conducted by adding a strong base directly to the product reaction mixture of step 2 without separation of the product of formula C from the reaction mixture. The treatment, can of course, also be applied to the isolated product of formula C. Typically this treatment is conducted at temperatures in the range of about from 0° to 100° C, preferably about from 20° to 60° C for from ½ hour to three hours, and preferably about from ½ hour to one hour. However, temperatures and reaction times both above and below these ranges can also be used. Suitable strong bases which can be used include, for example, alkali metal hydroxides such as, for example, sodium hydroxide, potassium hydroxide and the like, and alkali metal alkoxides such as, for example, sodium methoxide, potassium methoxide, and alkyl or aryl lithium such as butyl lithium, octyl lithium, phenyl lithium and the like. Suitable inert organic solvents include, for example, monoglyme, ethyle ether, benzene and the like.

Step 4 can be conducted by treating the intermediate product of formula II, of the invention, with the desired $R^1$, $R^2$ amine or amino derivative or N-heterocyclic derivative, including amines incorporated in cyclic systems. For example by treating the compound of formula II with an alcoholic solution of ammonia, the corresponding compounds of formula I wherein each of $R^1$ and $R^2$ is hydrogen is obtained. Similarly, treatment with a monosubstituted amine will yield the corresponding compound of formula I wherein one of $R^1$ or $R^2$ is the corresponding substituent and the other is hydrogen, and where a disubstituted amine is used, one of $R^1$ or $R^2$ will correspond to each of the amine substituents. Correspondingly, using a nitrogen heterocyclic such as, for example, piperidine; pyrrolidine; or morpholine will afford the corresponding $N_1$-piperidino;

ture of the product of formula I is obtained (for example, where racemic glycerol acetonide mixture has been used to prepare the starting material of formula A, the respective optically active (+) and (−) isomers can be resolved, if desired, by conventional procedures. For example, by reacting the compounds of formula I with an optically active acid which will yield a mixture of optical salts of the compounds of formula I which can be resolved by conventional procedures (e.g. crystallization) into the respective (+) and (−) optical salts.

The 5- and 4-aminocarbonyl substituted starting materials of formula A can be conveniently prepared according to either of the following reaction sequences:

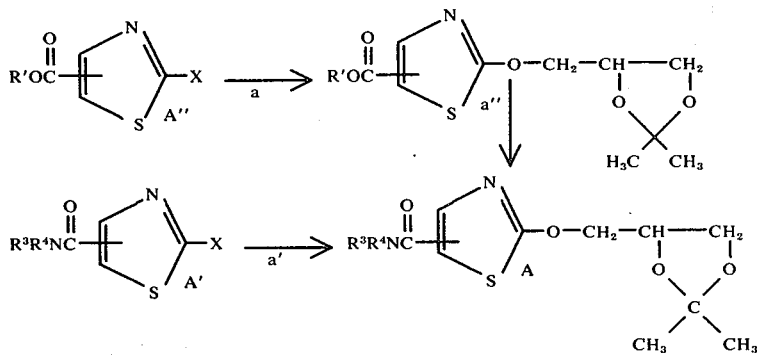

$N_1$-pyrrolidinyl; or $N_1$- morpholino compounds of formula I, respectively. Further, although optimum conditions and solvents will vary with the particular intermediate of formula II and ammonia or amino-type derivatives used, the treatment is typically conducted at temperatures in the range of about from 25° to 100° C for about from 10 minutes to 18 hours. However, temperature ranges both above and below these can also be used. Suitable solvents which can be used include, for example, monoglyme, methanol, ethanol, pyridine and the like.

Also although not specifically stated, it should be understood, as would be apparent to one having ordinary skill in the art, that where the starting material for a given step has free hydroxy or free amino groups, which could interfere with the treatment, such groups are preferably protected with conventional labile ester or ether groups by procedures which are well within the scope of the art. For exaple, with respect to step 2, free hydroxy groups, other than the 1- and 2-hydroxy propane groups, are conveniently protected by treatment with acetic anhydride. The acetate protecting group can then be conveniently removed, after the treatment of step 2, via treatment with a mild base.

Preferably, with the exception of step 3 which, as noted above, is conveniently conducted by direct addition to the product reaction mixture of the preceding step, the respective products of each step are isolated prior to their subsequent use as starting materials for the next succeeding step. Separation and isolation can be effected by any suitable separation or purification procedure such as, for example, evaporation, crystallization, chromatography, thin-layer chromatography, etc. Specific illustrations of typical separation and isolation procedures can be had by reference to the corresponding examples described herein below. However, other equivalent separation or isolation procedures could, of course, also be used. Where an isomer mixwherein X is chloro or bromo, R' is lower alkyl and preferably ethyl.

Steps a and a' of the above process can be effected by treating the respective thiazole compound of formula A or A'' with glycerol acetonide in a suitable inert solvent, in the presence of an alkali metal hydride. Typically, this treatment is conducted at temperatures in the range of about from 20° C to reflux for about from a few minutes to 20 hours, using mole ratios in the range of about 1 to 100 moles of glycerol acetonide per mole of compound A' or A''. However, temperatures, reaction times, and mole ratios both above and below can also be used. Suitable alkali metal hydrides which can be used include, for example, sodium hydride, potassium hydride, calcium hydride, lithium hydride and the like. Suitable inert organic solvents which can be used include, for example, monoglyme, tetrahydrofuran, diglyme, dimethylformamide, and the like. Also an excess of glycerol acetonide can be used as the solvent. Further by using the optically pure (+) glycerol acetonide isomer (see *J. Biol. Chem.*, v. 128, p. 463 (1939)) or the optically pure (−) glycerol acetonide isomer (see *J. Am. Chem. Soc.*, v. 67, p. 944 (1945)), the corresponding (+) or (−) optically active isomer of formula A or A''' is obtained. Correspondingly wherein a (+) or (−) isomer mixture of the glycerol acetonide is used, the product will similarly be a mixture of isomers. This optically active isomer relationship between the starting materials and products exist throughout all the steps of various processes described herein. Also typically and conveniently, a racemic glycerol acetonide isomer mixture will be used and thus typically the product will correspondingly be a racemic mixture. The starting materials of formula A'' can be prepared according to known procedures such as, for example, described in *Helv. Chim. Acta.*, p. 2057 (1954) and *Helv. Chim. Acta.*, p. 1073 (1942). The starting materials of formula A' and also the starting materials of formula A'' can be prepared according to the procedures set forth in the respective preparations described herein below or by obvious modifications of such procedures.

Step a'' can be conveniently effected by treating the compound of formula A''' with ammonia or an amine derivative having the desired $R^3,R^4$ groups. Typically, this treatment is conducted in a suitable inert organic solvent at temperatures in the range of about from 0° to 100° C, preferably about from 20° to 50° C for about from one to 48 hours, prefeably about from two to 10 hours. Typically a 10–50 molar excess of the desired amine is used. Suitable amines which can be used include, for example, methylamine, ethylamine, 4'-methylhexylamine, N-methyl-N-4'-methylhexylamine, 5'-methylhexylamine, n-dodecylamine, cycloheptylamine, 12'-hydroxydodecylamine, hexylamine, heptylamine, dimethylamine, N-methyl-N-5'-methlhexylamine, N-heptyl-N-methylamine, γ-cyclopentylpropylamine, β-cyclopentylethylamine, 4-cyclopentylbutylamine, dicycloheptylamine and the like. Suitable inert organic solvents which can be used include, for example, methanol, ethanol, glyme, and the like.

The starting materials of formula A where Z is

series can also be prepared according to the following procedure represented by the following schematic overall reaction equation sequence:

catalysts which can be used include, for example, Raney nickel, palladium, and the like. The 5- or 4-nitrothiazole starting materials can be prepared by treating the corresponding 2-chloro- or 2-bromo-5- or 4-nitrothiazole (*Helv. Chim. Acta.*, v. 33, p. 306 (1950)) with glycerol acetonide as described above. Step b'' of the above reaction sequence can be effected in two phases. In the first phase the 4- or 5-amino compound of formula A* is treated with sodium hydride in an inert organic solvent containing a catalytic amount of t-butanol. Typically, this treatment is conducted at temperatures in the range of about from 0° to 20° C, for about from one to 24 hours and preferably about from seven to eight hours. Best results are obtained by conducting this treatment under anhydrous conditions and preferably under an inert gaseous atmosphere. In the second phase the desired $R^4$-substituted chloroformate is then conveniently added to the reaction mixture, without separation of the intermediate product, and the mixture maintained at from about −10° to 80° C, preferably at reflux, for from about ½ hour to 16 hours. Suitable alkyl chloroformates which can be used include, for example, A'-methylhexyl chloroformate, 5'-methylhexyl chloroformate, γ-cyclopentylpropyl chloroformate, β-cyclohexylethyl chloroformate, n-heptyl chloroformate, and the like. Alternatively, step b'' can be effected by treating the 4- or 5-amino compound of formula A* with the desired $R^4$-substituted chloroformate in an inert organic basic solvent. Typically this treatment is conducted at temperatures in the range of about from 0° to 30° C for about from one to

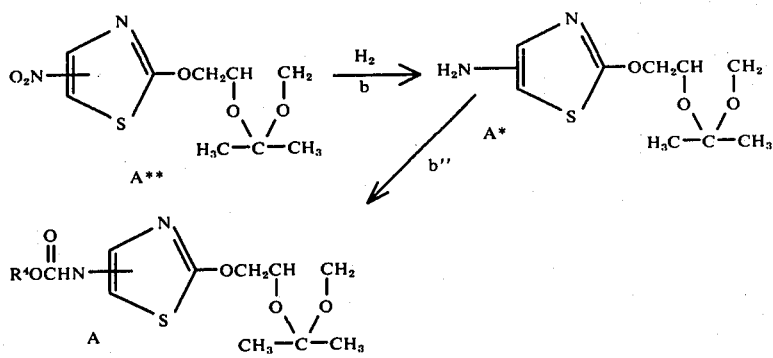

wherein $R^4$ is as defined herein above.

As shown above, the 4- or 5-amino compounds of formula A can be prepared from the corresponding 4- or 5-nitro compounds of formula A via hydrogenation. This can be conveniently effected by treating the nitro compound of formula A** in a suitable inert organic solvent with gaseous hydrogen in the presence of a suitable catalyst such as, for example, Raney nickel. This treatment is typically conducted at temperatures in the range of about from −30° to +30° C, preferably about from 25° to 30° C, for about from 15 minutes to 16 hours and preferably about from one to three hours. Suitable solvents which can be used include, for example, ethanol, methanol, ethyl acetate, tetrahydrofuran, and the like. Suitable hydrogenation 24 hours. The same range of alkyl chloroformates can be used in this treatment as above. Suitable basic solvents include, for example, pyridine, triethylamine and the like.

The

starting materials of formula A can also be prepared starting from the known $R^3$-carboxylic acid ethyl ester (*Helv. Chim. Acta.*, v. 29, p. 1230 (1946)) according to the sequence represented by the following schematic reaction equations:

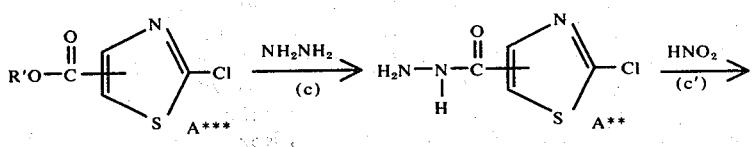

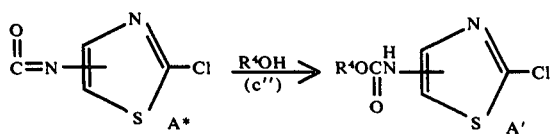

wherein R' is lower alkyl, aryl or arylalkyl and R⁴ is as defined herein above for Z is

Step c of the above reaction sequence can be effected by treating the above 2-chloro-4- or 5-carboxylic acid or alkyl ester compound of formula A* with monohydrazine hydrate. Typically, this treatment is conveniently conducted at temperatures in the range of about from 0° to 100° C, for about from one to six hours. Suitable inert organic solvents which can be used include, for example, methanol, ethanol, monoglyme, dimethylformamide and the like. Step c' is effected in two steps, first by treating the 4- or 5-hydrazide product of step c (formula A) with nitrous acid. The nitrous acid can be conveniently prepared by reacting sodium nitrite and conc. hydrochloric acid. The treatment (step c' (1)) is conveniently conducted at ambient temperatures although temperatures both above and below ambient can also be used. The resulting 4- or 5-azido-2-chlorothiazole is then heated (step c' (2)) at temperatures in the range of about from 60° to 150° C under anhydrous conditions in a suitable inert organic solvent; to give the 4-or 5-isocyanate of formula A*. Suitable inert organic solvents which can be used include, for example, benzene, toluene, xylene, diglyme, triglyme, and the like, and mixtures of such solvents.

Step c can be effected by treating the compounds of formula A* with an alcohol of the desired R⁴ group. Typically, and preferably, this treatment is conducted at temperatures in the range of about the reflux temperature of the system, for about from ½ hour to 5 hours. Suitable alcohols which can be used include, for example, heptanol, 5'-methylhexanol, 4'-methylhexanol, β-cyclohexylethanol, γ-cyclohexylpropanol and the like. Alternatively, the treatment can be conducted in an inert organic solvent such as, for example, monoglyme, dioxane, benzene, and the like.

The starting material of formula A can then be prepared by treating the 2-chloro compounds of formula A with glycerol acetonide as described above.

Although the starting materials of formula A wherein Z is

can be prepared according to conventional procedures and procedures described in the parent application Ser. No. 289,730, filed Sept. 15, 1972, or by obvious modifications thereof, much higher yields of this group of starting materials can be obtained by using the procedure of Berkoz, Edwards and Fried described in U.S. Ser. No. 451,194, filed on Mar. 14, 1974, and which procedure can be represented by the following overall reaction sequence and description:

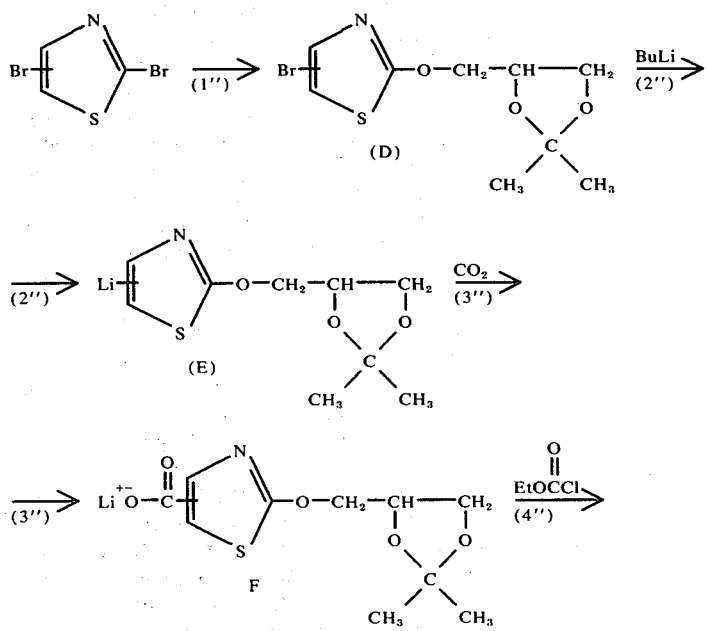

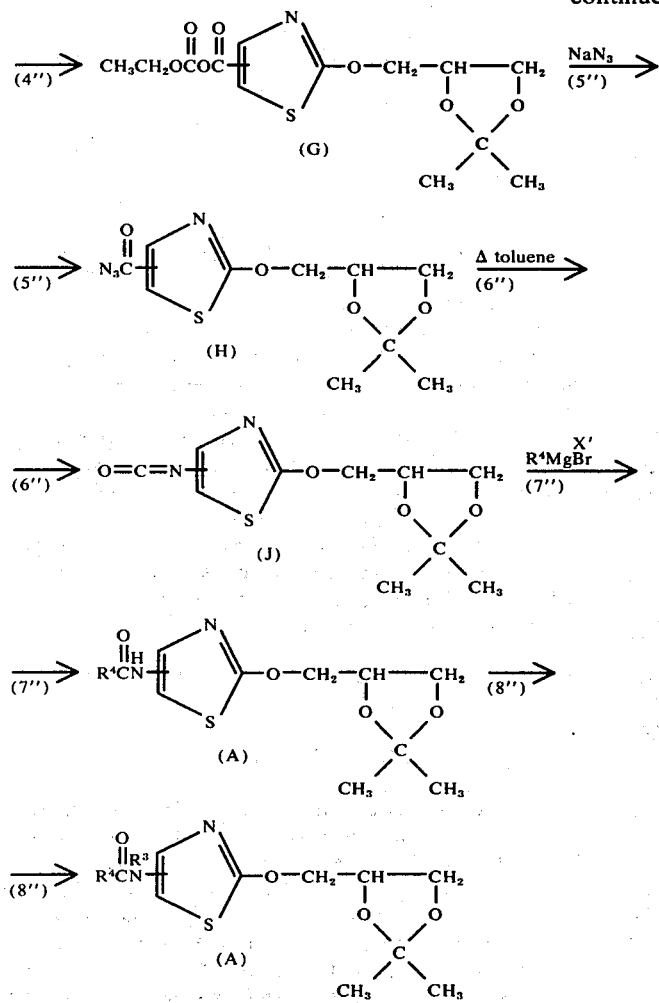

wherein X' is chlor, bromo or iodo; and R³ and R⁴ are as defined above.

Step 1″ of the above process can be conveniently effected by treating the 2,4-dibromothiazole or 2,5-dibromothiazole starting material with glycerol acetonide, in a suitable inert organic solvent in the presence of an alkali metal hydride in the same manner as described herein above with respect to the preparation of other 4′ -or 5′ -position substituted thiazol-2-oxy-propanediol 1,2-acetonides. The 2,5-dibromothiazole and 2,4-dibromothiazole are known compounds and can be prepared according to procedures described in *Recueil des Travaux Chimiques des Pays Base*, volume 73, page 325 (1964) and the 2,4-dibromothiazole in *Bulletin de la Societe Chimique de France*, page 1735 (1962), respectively.

Step 2″ can be effected by treating the compound of formula D with an alkyl lithium reagent (preferably t- or n-butyllithium) in a suitable inert organic solvent. Typically this treatment is conducted at temperatures in the range of about from −10° to −150° C, preferably about from −60° to −80° C for about from 10 minutes to 2 hours, and preferably about from 15 minutes to 1 hour, using mole ratios in the range of about from two to three moles of alkyl lithium per mole of the compound of formula D. Best results are typically obtained by conducting the treatment under anhydrous conditions and preferably in the absence of air, e.g. by conducting the treatment under an inert gas such as nitrogen. Suitable inert organic solvents which can be used include, for example, tetrahydrofuran, hexane, diethyl ether, monoglyme, and mixtures of such solvents and the like.

Step 3″ can be conveniently conducted in situ by bubbling anhydrous carbon dioxide through the reaction product solution of the compound of formula E. The carbon dioxide reaction is typically conducted at temperatures in the range of about from −78° C to room temperature and since the rate of reaction will vary with the flow rate of carbon dioxide, the reaction is preferably monitored by thin-layer chromatography and allowed to proceed until the thin-layer chromatography reveals that 3-(thiazol-2-oxy)-propanediol acetonide derived from the starting material of formula E has been consumed.

Step 4″ is also conveniently conducted in situ by adding an alkyl chloroformate directly to the reaction medium. Typically this step is conducted at temperatures in the range of about from −78° C to room temperature for about from one hour to six hours. Suitable alkyl chloroformates which can be used include, for example, methyl chloroformate, ethyl chloroformate, isopropyl chloroformate, t-butyl chloroformate, n-butyl chloroformate and the like. Best results are typically obtained using ethyl chloroformate. Acccordingly the above reaction sequence has been shown using ethyl chloroformate although other alkyl chloroformates could also be used. Also typically about from 1.1 to 1.5 moles of alkyl chloroformate is used per mole of compound of formula F.

Step 5" is also conveniently conducted in situ by adding sodium azide, preferably as an aqueous solution, directly to the product reacton mixture of formula G. Typically this step is conducted at temperatures in the range of about from 0° C to room temperature, preferably about from 10° to 25° C, for about from ½ hour to 6 hours, preferably about from ½ hour to two hours.

Step 6" is conveniently effected by adding the compound of formula H to an inert aromatic solvent, such as toluene, and heating the mixture at temperatures in the range of about from 100° to 110° C, preferably about from 105°–108° C, for about from ½ hour to two hours. Also while best results are obtained using these conditions, temperatures and raction times, both above and below these ranges could also be used. Also other inert solvents such as, for example, xylene and diglyme could also be used.

Step 7" can be conveniently effected by a Grignard type reaction by treating the isocyanate product of formula J with a Grignard reagent having the desired $R^4$-substituents. Typically this treatment is conducted at temperatures in the range of about from −78° to −100° C, preferably about −78° C, for about from one minute to ½ hour and preferably about from one minute to 15 minutes. Typically the treatment is conducted in an inert solvent such as, for example, toluene, ether (diethyl), tetrahydrofuran, monoglyme and the like, or mixtures thereof. Suitable Grignard reagents which can be used are those haviing the general formula $R^4MgX'$ wherein $X'$ is chloro, bromo or iodo and $R^4$ is as defined herein, such Grignard reagents include, for example, methylmagnesium chloride, t-butylmagnesium bromide, 5'; -methylhexylmagnesium bromide; 4'-methylhexylmagnesium bromide; methylmagnesium iodide; butylmagnesium chloride; γ-cyclopentylpropylmagnesium bromide; dodecylmagnesium bromide and the like. The Grignard reagent can be prepared according to known procedures, or obvious modifications thereof such as, for example, described in Fieser & Fieser, *Reagents for Organic Synthesis*, pages 415–424 (1967), John Wiley & Sons, Inc.

Where the $R^3$-substituted compounds are desired, step 8" can be conveniently conducted in two phases by first treating the $R^3$-substituted compound of formula A with a strong base such as butyllithium, t-butyllithium, sodium hydride, or potassium t-butoxide, in an inert organic solvent under anhydrous condition. Typically this treatment is conducted at temperatures in the range of about from −70° to −85° C for about from five minutes to two hours, using about from 1 to 1.5 moles of strong base per mole of compound of formula A. Suitable inert organic solvents which can be used include, for example, tetrahydrofuran, diethyl ether and the like. The second phase is conducted in situ by adding the desired reagent having the formula $R^3X'$ wherein $R^3$ and $X'$ are as defined above, preferably in an aprotic solvent (e.g. ether, tetrahydrofuran, monoglyme, dimethylformamide) to the product reaction mixture and then allowing the resulting mixture to warm to about room temperature. This phase is typically conducted at temperatures of about from −78° to 25° C, conveniently room temperature, for about from ½ hour to two hours. Suitable $R^3X'$ reagents include, for example, methyl iodide, ethyl bromide, phenyl chloride, propyl iodide, 5'-methylhexyl chloride and the like. The $R^3X'$ reagents can be prepared according to conventional procedures, well known to the art, or by obvious modifications of such procedures.

The starting materials of formula A wherein Z is

can be advantageously prepared according to the procedure described by Berkoz, Edwards and Fried, in the aforementioned U.S. application Ser. No. 451,194, via the following overall reaction sequence:

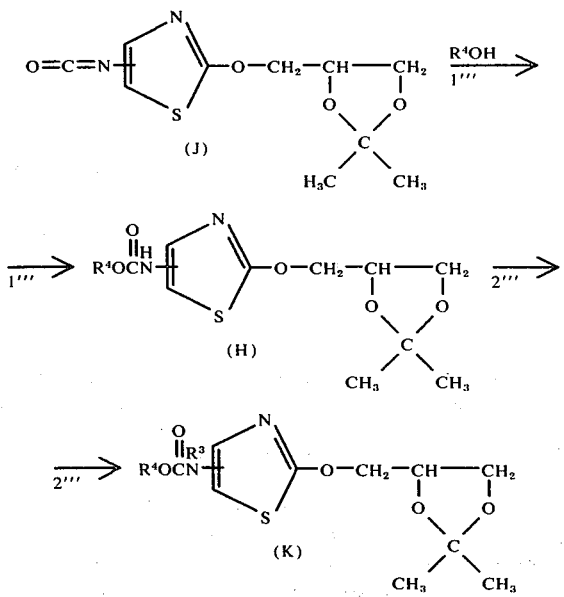

wherein $R^3$ and $R^4$ are as defined herein above.

Step 1''' can be effected by treating the compound of formula J with an alcohol having the desired $R^4$ group - i.e. $R^4OH$. Although the treatment can be conducted without a solvent, the treatment is typically conducted in an inert organic solvent such as, for example, toluene, since this simplifies isolation of the resulting product. The treatment is typically conducted at temperatures in the range of about from 95° to 120° C for about from ½ to four hours, preferably about 1 to 2 hours. Typically a stoichiometrical excess of alcohol is used, for example, a 10–20 mole equivalent excess can be conveniently used. Suitable $R^4OH$ alcohols which can be used include, for example, 5-methylhexyl alcohol; 4-methylhexyl alcohol; methanol; phenol, γ-cyclophenylpropyl alcohol; dodecyl alcohol and the like.

Where the $R^3$-substituted compounds are desired, step 2''' can be conveniently conducted in two phases by first treating the $R^3$-substituted compound of formula A with a strong alkali such as butyllithium, t-butyllithium, or sodium hydride, in an inert organic solvent under anhydrous condition. Typically this treatment is conducted at temperatures in the range of about from −70° to −85° C for about from ½ hour to 2 hours, using about from 1 to 1.5 moles of strong alkali per mole of compound of formula A. Suitable inert organic solvents which can be used include, for example, tetrahydrofuran, diethyl ether and the like. The second phase is conducted in situ by allowing the product reaction mixture to warm to about room temperature and then adding the desired reagent having the formula R³X′ wherein R³ and X′ are as defined above, preferably in an aprotic solvent (e.g. ether, tetrahydrofuran, dimethylformamide, monoglyme, etc.). This phase is typically conducted at temperatures of about from 15° to 30° C, conveniently room temperature, for about from ½ to 2 hours. Suitable R³X′ reagents include, for example, methyl chloride, ethyl bromide, phenyl chloride, propyl iodo, 5′-methylhexyl chloride and the like. The R³X′ reagents can be prepared according to conventional procedures, well known to the art, or by obvious modifications of such procedures.

The compounds of formula III can be prepared directly from the corresponding compounds of formula I:

include, for example, formaldehyde, acetone, cyclohexanone, cyclopentanone, cycloheptanone, and the like. Also aluminum t-butoxide can be used in place of aluminum isopropoxide.

Alternatively the above treatment can be effected in the case of the 2-spirocycloalkyloxazolidine compounds, of formula III (i.e. R⁵ and R⁶ together with the carbon atom to which they are joined form a cycloalkyl), by treating the corresponding compound of formula I′ with a cycloalkanone having the desired cycloalkyl group, in an inert organic solvent in the presence of potassium carbonate. Typically this treatment is conducted at temperatures in the range of about from 20° to 100° C for about from 48 to 72 hours, using mole ratios in the range of about from one to 150 moles of cycloalkanone per mole of compounds of formula I′. Suitable cycloalkanones which can be used include, for

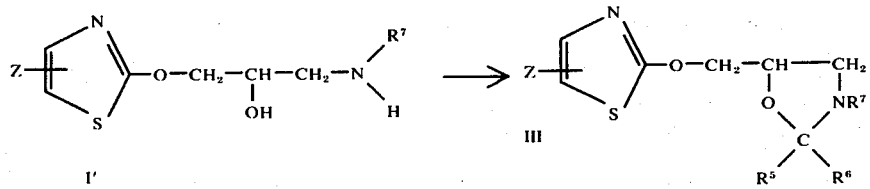

wherein R⁵, R⁶, R⁷ and Z are as defined herein above.

This treatment can be conveniently effected by treating the corresponding compound of formula I′ with a ketone or aldehyde having the desired R⁵ and R⁶ substituents, and aluminum isopropoxide. Typically this treatment is conducted at temperatures in the range of about from 20° to 100° C for about from one to 48 hours using mole ratios in the range of about from one to 150 moles of ketone and one to 10 moles of aluminum isopropoxide per mole of compound of formula I.

Typically a substantial excess of ketone or aldehyde is used as the excess usually will function as an inert organic solvent. Suitable ketones which can be used example, cyclohexanone, cyclopentanone, cycloheptanone, and the like. In place of potassium carbonate, the following compounds can also be used; sodium carbonate, lithium carbonate, and the like.

The compounds of formula III, and of formula I, wherein Z is the group

and one of R¹ or R² is hydrogen and the other is hydrogen, lower alkyl, or arylalkyl, can also be prepared via the process of the invention, represented by the following schematic overall reaction equations:

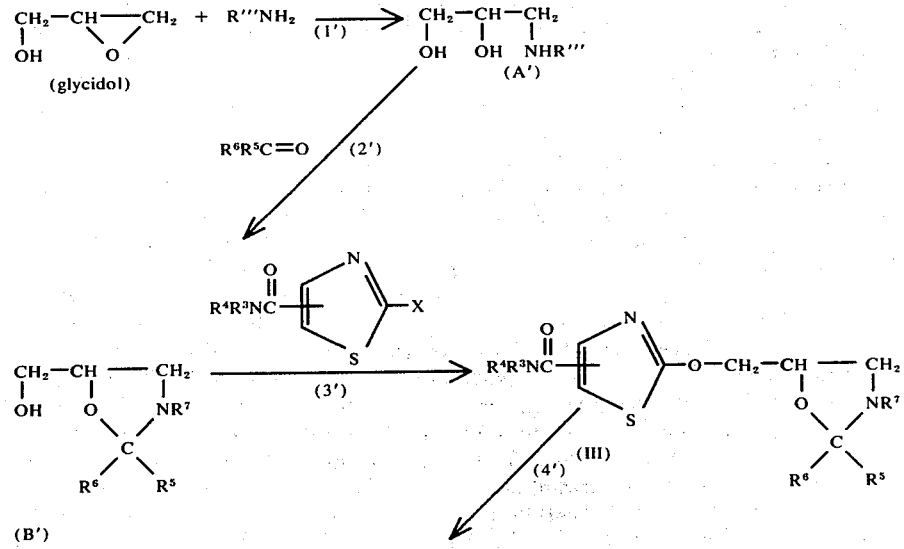

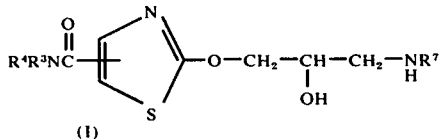

wherein R''' is hydrogen, lower alkyl, aryl, or arylalkyl, X is chloro or bromo, and $R^3$, $R^4$, $R^5$, $R^6$ and $R^7$ are as defined herein above.

Step (1') of the above process can be effected by treating glycidol with ammonia or the desired monosubstituted amine. Typically, this treatment is conducted at temperatures in the range of about from 20° C to reflux and preferably at reflux, for about from 0.5 to five hours. Frequently, as the reaction is exothermic and typically will occur at ambient temperature, the reaction can be conducted at reflux without supplying external heat. Also wherein anhydrous ammonia or volatile amines are used, the reaction is typically conducted by passing the gaseous ammonia or substituted amine through a solution of glycidol. Alternatively, suitable inert organic solvents can be used but, typically are unnecessary as glycidol itself is a liquid at room temperature in which the respective substituted amines are usually soluble. Suitable substituted amines which can be used include, for example, methylamine, ethylamine, propylamine, isopropylamine, n-butylamine, t-butylamine, phenylethylamine, p-methylbenzylamine and the like.

Step (2') can be effected by treating the product of step (1'), of formula A', with an aldehyde or ketone in a suitable inert organic solvent such as, for example, ethanol. Typically, this treatment is conducted at temperatures in the range of about from 20° C below reflux to reflux and preferably at reflux about from 8 to 18 hours. Typically, formaldehyde is used in the form of an aqueous solution.

Step (3') is preferably conducted in two steps. In the initial phase the 5-hydroxymethyl-3-oxazolidine or 5-hydroxymethyl-substituted oxazolidine product of step (2') (i.e. formula B') is treated with an alkaline metal hydride, e.g. sodium hydride, in a suitable inert organic solvent. Typically, this treatment is conducted at temperatures in the range of about from 20° to 80° C for about from 15 minutes to five hours. Preferably this treatment is conducted under anhydrous conditions and preferably conducted in the absence of air, e.g. under an inert gas, e.g. nitrogen. Inert organic solvents which can be used include, for example, dimethylformamide, monoglyme, diglyme, and the like. The second phase of step (3') is conducted by treating the initial product reaction mixture with the desired substituted-2-chloro or 2-bromothiazole. Typically, this treatment is conducted at temperatures in the range of about from 60° to 140° C for about from one to 24 hours. Typically, the 2-halothiazole reagent is added to the reaction mixture in the form of a solution in a suitable inert organic solvent. Suitable inert organic solvents which can be used include, for example, dimethylformamide, monoglyme, diglyme, and the like. Also an excess of the oxazolidine reagent can typically be used as the solvent. Again preferably the second phase will also be conducted under anhydrous conditions and preferably conducted in an inert gas such as, for example, nitrogen.

Step (4') can be conveniently effected by simple acidic or basic hydrolysis of the intermediate of formula III. Thus, acid hydrolysis can be conveniently effected by treating the compound of formula III with a suitable organic acid such as, for example, acetic, formic, oxalic acid and the like or suitable acids such as, for example, hydrochloric, sulfuric, and the like. Preferably the hydrolysis is conducted under mildly acidic conditions. Similarly, basic hydrolysis can be conducted by treating the compound of formula III with a suitable base such as, for example, dilute sodium hydroxide, potassium hydroxide and the like. Preferably the hydrolysis can be conducted under mildly alkaline conditions. Alternatively, the hydrolysis can be conducted via exchange with a suitable ion exchange resin in either the $H^+$ or $OH^-$ form.

Again, as noted previously with respect to the first described process of the invention, it should be understood that in each of the aforedescribed preparation and process steps, that where starting materials having free amino or free hydroxy groups which could interfere with the desired treatments are used, such starting materials are first protected with conventional labile ester or ether groups. And again, unless noted to the contrary, it is preferred that the respective products of each process step or preparation step, described herein above, be separated and/or isolated prior to its use as starting material for subsequent steps. Separation and isolation can be effected by any suitable purification procedure such as, for example, evaporation, crystallization, column chromatography, thin-layer chromatography, distillation, etc. Specific illustrations of typical separation and isolation procedures can be had by reference to the appropriate examples described herein below. However, other equivalent separation procedures could, of course, also be used. Also where an isomer mixture of the product of formula I or III is obtained (for example, wherein an isomeric mixture of glycerol acetonide has been used in steps 1 and 1', respectively), the respective optically active (+) and (−) isomers can be resolved by known procedures. Optimum resolution procedures can be obtained by routine trial and error procedures well within the scope of those skilled in the art.

The pharmaceutically acceptable acid addition salts of the compounds of formulas I and III can be prepared via neutralization of the parent compound, typically via neutralization of an amino moiety, with the desired acid. Other pharmaceutically acceptable addition salts can then be conveniently prepared from the neutralization addition salts via anion exchange with a suitable ion exchange resin in the desired anion form.

The compounds of formulas I and III, of the invention, are useful in the treatment and palliation of cardiovascular abnormalities in mammals. These compounds primarily achieve their therapeutic action by selectively blocking the cardiac β-adrenergic receptor sites and accordingly, because they are cardiac selective, they can also be applied to treat cardiac abnormalities in patients suffering from asthma or chronic obstructive lung disease. The compounds are especially useful in the treatment or palliation of cardiac arrhythmias, angina pectoris, hypertrophic subaortic stenosis, pheochromocytoma, thyrotoxicosis, hyperkinetic syndromes, tetralogy of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication (i.e. nitroglycerin) presently commonly used in the treatment of angina pectoris has no recognized prophylactic action.

Additional information concerning the use, action and determination of β-blockers can be obtained by reference to the literature such as, for example, Dotlery et al, *Clinical Pharmacology and Therapeutics*, volume 10, No. 6, 765–797 and the references cited therein.

The compounds of formulas I and III can be administered in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the pharmaceutically acceptable salts of the compounds of formula I and/or III and a pharmaceutical carrier. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents.

The solid compositions can take the forms of tablets, powders, capsules, pills or the like, preferably in unit dosage forms for simple administration or precise dosages. Suitable solid carriers include, for example, pharmaceutical grades of starch, lactose, sodium saccharin, sodium bisulfite and the like.

The compounds of this invention are typically administered in dosages of about from 0.01 to 5 mg. per kg. of body weight. The precise effective dosage will, of course, vary depending upon the mode of administration, the condition being treated and the host. Preferably, the compounds are administered orally, either as solid compositions, e.g. tablets, or liquids as described herein above.

A further understanding of the invention can be had from the following non-limiting Preparations and Examples. Also as used herein above and below unless expressly stated to the contrary, all temperatures and temperature ranges refer to the Centigrade system and the terms ambient or room temperature refer to about 20° C. The term percent or (%) refers to weight percent. The term equivalent refers to a quantity of reagent equal in moles to the moles of the preceding or succeeding reactant recited in that Preparation or Example in terms of moles or finite weight or volume. Also unless expressly stated to the contrary, racemic mixtures are used as starting materials and correspondingly racemic mixtures are obtained as products and where necessary, preparations and examples are repeated to provide sufficient quantities of starting materials for subsequent preparations and examples.

PREPARATION 1

2-Bromo-5-alkoxycarbonylthiazole

A mixture containing 272 g. of methyl chloroacetate and 158 g. of methyl formate in 600 ml. of toluene is cooled to 0° C. A total of 143 g. of sodium methoxide is added portionwise, maintaining the temperature of the mixture below 5° C, with rapid stirring. The mixture is then stirred for an additional 4 hours at 0° C and one liter of water then added yielding a two phase liquid-liquid mixture. The toluene layer is decanted off and the aqueous layer is then washed with ethyl ether and neutralized with dilute aqueous hydrochloric acid and extracted with ethyl ether. The ethyl ether extracts are combined, dried over magnesium sulfate and then evaporated yielding the oil residue of methyl chloroformyl acetate. 210 Grams of thiourea in 1500 ml. of ethanol is then added to the residue and refluxed for 18 hours. The ethanol solvent is then distilled off and one liter of water added to the concentrate. The aqueous mixture is then filtered and the filtrate made slightly basic by the addition of dilute aqueous ammonium hydroxide yielding a precipitate which is then recovered by filtration, washed with water, and dried, under vacuum, for 18 hours at 70° C yielding 2-amino-5-methoxycarbonylthiazole.

A mixture containing 100 g. of amyl nitrate and 600 ml. of bromoform is warmed to 70° C and then a total of 100 g. of 2-amino-5-methoxycarbonylthiazole is added portionwise with rapid stirring while maintaining the temperature at about 95–100° C. The mixture is then stirred for an additional 10 minutes at this temperature and then the bromoform is distilled off under vacuum. The residue is chromatographed on silica gel yielding 2-bromo-5-methoxycarbonylthiazole.

Similarly, 2-bromo-5-ethoxycarbonylthiazole is prepared by following the same procedure but using ethyl chloroacetate and sodium ethoxide in place of methylchloroacetate and sodium methoxide.

2-Bromo-4-methoxycarbonylthiazol and 2-bromo-4-ethoxycarbonylthiazole are respectively prepared by following the procedure described in *Helv. Chim. Acta.*, v. 25, p. 1432 (1942); ibid., v. 28, 362 (1945) and ibid., v. 27, p. 1432 (1944).

PREPARATION

2-Bromo-5-substituted aminocarbonylthiazole

A mixture containing 10 g. of 2-bromo-5-methoxycarbonylthiazole, 10 ml. of 5'-methylhexylamine, 12 ml. of water and 50 ml. of methanol is stirred for 18 hours at room temperature. The mixture is then evaporated to remove methanol and poured into 500 ml. of ethyl acetate, which is then washed three times with water, then dried over magnesium sulfate and evaporated to dryness. The residue is then redissolved and recrystallized from ethyl acetate affording 2-bromo-5-(5'-methylhexylaminocarbonyl)-thiazole.

Similarly, by following the same procedure but respectively replacing 5'-methylhexylamine with 4'-methylhexylamine, 3'-methylhexylamine, 4'-ethylhexylamine, 3'-propylhexyl, cyclopentylamine, β-cyclopentylethyl, γ-cyclo-pentylpropyl, 4'-cyclopentylbutylamine, γ- cyclohexylpropyl, n-heptylamine, cycloheptylamine, n-octylamine, n-nonylamine, n-dodecylamine, 7'-hydroxy-n-heptylamine, 9'-acetoxy-n-nonylamine, β-methoxyethylamine, di(γ-cyclopentylpropyl) -cyclopentylpropyl) amine, di(n-dodecyl)amine, hexylamine, methylamine, dimethylamine, isopropylamine, aqueous ammonia, and benzylamine the following compounds are respectibely prepared:

2-bromo-5-(4'-methylhexylaminocarbonyl)-thiazole;
2-bromo-5-(3'-methylhexylaminocarbonyl)-thiazole;
2-bromo-5-(4'-ethylhexylaminocarbonyl)-thiazole;
2-bromo-5-(3'-propylhexylaminocarbonyl)-thiazole;
2-bromo-5-cyclopentylaminocarbonylthiazole;
2-bromo-5-(β-cyclopentylethylaminocarbonyl)-thiazole;
2-bromo-5-(γ-cyclopentylpropylaminocarbonyl)-thiazole;
2-bromo-5-n-heptylaminocarbonylthiazole;
2-bromo-5-(4'-cyclopentylbutylaminocarbonyl)-thiazole;
2-bromo-5-(γ-cyclohexylpropylaminocarbonyl)-thiazole;
2-bromo-5-cycloheptylaminocarbonylthiazole;
2-bromo-5-octylaminocarbonylthiazole;
2-bromo-5-nonylaminocarbonylthiazole;
2-bromo-5- dodecylaminocarbonylthiazole;
2-bromo-5-(7'-hydroxyheptylaminocarbonyl)-thiazole;
2-bromo-5-(9'-acetoxynonylaminocarbonyl)-thiazole;
2-bromo-5-(β-methoxyethylaminocarbonyl)-thiazole;
2-bromo-5-di-(γ-cyclopentylpropyl)-aminocarbonylthiazole;
2-bromo-5-di-(n-dodecyl)-aminocarbonylthiazole;
2-bromo-5-hexylaminocarbonylthiazole;
2-bromo-5-methylaminocarbonylthiazole;
2-bromo-5-dimethylaminocarbonylthiazole;
2-bromo-5-isopropylaminocarbonylthiazole;
2-bromo-5-aminocarbonylthiazole; and
2-bromo-5-benzylaminocarbonylthiazole.

Similarly, by following the same procedure but using 2-bromo-4-methoxycarbonylthiazole in place of 2-bromo-5-methoxycarbonylthiazole, the corresponding 4-position isomers of each of the above products is respectively prepared.

PREPARATION 3

2-Bromo-5-carboxythiazole

A mixture containing 10 g. of 2-bromo-5-methoxycarbonylthiazole, 100 ml. of 10% aqueous sodium hydroxide and 200 ml. of methanol is stirred at 0° C for 5 minutes. The methanol is distilled off in vacuo and the resulting concentrate extracted twice with ethyl acetate. The remaining aqueous phase is acidified by the careful addition of dilute aqueous hydrochloric acid resulting in the formation of a precipitate which is then recovered by filtration and dried under vacuum yielding 2-bromo-5-carboxythiazole.

Similarly, 2-bromo-4-carboxythiazole is prepared according to the same procedure but using 2-bromo-4-methoxycarbonylthiazole in place of 2-bromo-5-methoxycarbonylthiazole.

PREPARATION 4

2-Bromo-5-substituted aminocarbonylthiazole.

A mixture containing 6 g. of 2-bromo-5-carboxythiazole, 3 ml. thionyl chloride, and 0.5 ml. of dimethylformamide in 150 ml. of ethyl acetate is refluxed for 30 minutes and then evaporated to remove the ethyl acetate solvent. The resulting residue is dissolved in 100 ml. of chloroform, then cooled to about 0° C. A mixture containing 10 ml. of t-butylamine in 100 ml. of chloroform is then added with stirring and the ensuing mixture warmed to 0° C, washed twice with water and then dried over magnesium sulfate and evaporated to dryness affording a solid residue of 2-bromo-5-t-butylaminocarbonylthiazole.

Similarly, 2-bromo-4-t-butylaminocarbonylthiazole is prepared by following the same procedure but using 2-bromo-4-carboxythiazole in place of the 5-position isomer. Similarly, by replacing t-butylamine with the amine reagents set forth in Preparation 2, the corresponding 2-bromo-4- and 5-substituted aminocarbonylthiazoles are respectively prepared.

PREPARATION 5

3-(5-Bromothiazol-2-oxy)-propendiol acetonide

In this preparation sodium hydride (18 g., 56 wt. % dispersion in oil) is washed with n-hexane, and the hexane is replaced with monoglyme (100 ml.) To this mixture is added a solution of glycerol acetonide (44.5 g.) is monoglyme (200 ml.) under an atmosphere of nitrogen. After 15 minutes, 2,5-dibromothiazole (32 g.) is added, and the mixture is refluxed for 1.25 hours. The reaction mixture is then cooled, diluted with ether and filtered. The filtrate is washed with saturated aqueous sodium chloride twice, dried and concentrated by evaporation. Fractional distillation yields 3-(5-bromothiazol-2-oxy)-propanediol 1,2-acetonide.

Similarly 3-(4-bromothiazol-2-oxy)-propanediol 1,2-acetonide is prepared by following the same procedure but replacing 2,5-dibromothiazole with 2,4-dibromothiazole.

EXAMPLE A 3-(5-Azidocarbonylthiazol-2-oxy)-propanediol 1,2-acetonide

Examples A-E, illustrate the preparation of acetonide intermediates according to the procedure of Berkoz, Edwards and Fried, described in U.S. Ser. No. 451,194, filed on Mar. 14, 1974.

In this example 150 ml. of n-butyllithium, in hexane, solution (each ml. of solution contains 100 mg. of butyllithium) is cooled to −78° C and then added to a solution containing 60 g. of 3-(5-bromothiazol-2-oxy)-propanediol 1,2-acetonide in 200 ml. of anhydrous tetrahydrofuran at −78° C under a nitrogen atmosphere. The resultant mixture is maintained at −78° C for 15 minutes affording 3-(5-lithiothiazol-2-oxy)-propanediol 1,2-acetonide. A stream of anhydrous carbon dioxide is then passed through the solution. The mixture is periodically sampled and monitored by thin-layer chromatography and the carbon dioxide treatment continued until all of the starting material is consumed (about two hours). Thirty grams of ethyl chloroformate is then added to the reaction mixture and the temperature of the resulting mixture allowed to rise to room temperature and allowed to stand at room temperature for three hours. An aqueous solution containing 50 g. of sodium azide in 100 ml. of water is then added and the resulting mixture stirred vigorously for 50 minutes. The tetrahydrofuran solvent is then distilled off at 50° C and the resulting residue is then washed with diethyl ether and then with water affording a crude residue of 3-(5-azidocarbonylthiazol-2-oxy)-propanediol 1,2-acetonide. The crude residue is then further purified by chromatography over aluminum oxide (neutral, activity III) eluting with a gradient system of 3,000 ml. of hexane and 3,000 ml. of benzene.

Similarly by following the same procedure but using 3-(4-bromothiazol-2-oxy)-propanediol 1,2-acetonide as the starting material, the corresponding 3-(4-azidocarbonylthiazol-2-oxy)-propanediol 1,2-acetonide is prepared.

EXAMPLE B

3-[5-γ-cyclopentylpropylcarbonylaminothiazol-2-oxy]-propanediol 1,2-acetonide

In this example a Grignard reagent is prepared by adding 5 g. of γ-cyclopentylpropyl bromide to a suspension of 700 mg. of magnesium in 100 ml. of anhydrous ethyl ether at room temperature under an argon atmosphere. The resulting exothermic reaction is allowed to go to completion affording a liquid mixture containing the Grignard reagent γ-cyclopentylpropylmagnesium bromide, which is then cooled and maintained at −78° C.

3-(5-Isocyanatothiazol-2-oxy)-propanediol 1,2-acetonide is prepared by adding 5.5 g. of 3-(5-azidocarbonylthiazol-2-oxy)-propanediol 1,2-acetonide to 100 ml. of anhydrous toluene. The mixture is then heated, under an argon atomsphere, at 108° C for 40 minutes. The resulting mixture is then cooled to −78° C and added to the γ-cyclopentylpropylmagnesium bromide diethyl ether solution previously prepared. The combined reaction mixture is allowed to react for one minute and then 2 ml. of water is added and the temperature of the mixture allowed to rise to room temperature. The resulting product mixture is then filtered, dried over sodium sulfate, filtered, and evaporated to dryness affording a residue which is then further purified by plate chromatography eluting with a system of 5% methanol-95% chloroform yielding 3-(5-γ-cyclopentylpropylcarbonylaminothiazol-2-oxy)-propanediol 1,2-acetonide.

Similarly by following the same procedure but substituting the appropriate Grignard reagents, the following compounds are respectively prepared:
3-(5-5'-methylhexylcarbonylaminothiazol-2-oxy)-propanediol 1,2-acetonide;
3-(5-3'-methylhexylcarbonylaminothiazol-2-oxy)-propanediol 1,2-acetonide;
3-(5-4'-methylhexylcarbonylaminothiazol-2-oxy)-propanediol 1,2-acetonide;
3-(5-4'-ethylhexylcarbonylaminothiazol-2-oxy)-propanediol 1,2-acetonide;
3-(5-3'-propylhexylcarbonylaminothiazol-2-oxy)-propanediol 1,2-acetonide;
3-(5-n-heptylcarbonylaminothiazol-2-oxy)-propanediol 1,2-acetonide;
3-(5-β-cyclopentylethylcarbonylaminothiazol-2-oxy)-propanediol 1,2-acetonide;
3-(5-4'-cyclopentylbutylcarbonylaminothiazol-2-oxy)-propanediol 1,2-acetonide;
3-(5-γ-cyclohexylpropylcarbonylaminothiazol-2-oxy)-propanediol 1,2-acetonide;
3-(5-methylcarbonylaminothiazol-2-oxy)-2-propanediol 1,2-acetonide;
3-(5-t-butylcarbonylaminothiazol-2-oxy)-propanediol 1,2-acetonide;
3-(5-n-hexylcarbonylaminothiazol-2-oxy)-propanediol 1,2-acetonide; and
3-(5-benzylcarbonylaminothiazol-2-oxy)-propanediol 1,2-acetonide.

Similarly by following the same procedure but using the corresponding 4-position isomers, the corresponding 4-position isomer is respectively prepared.

EXAMPLE C 3-(5-N'-methyl-γ-cyclopentylpropylcarbonylaminothiazol-2-oxy)-propanediol 1,2-acetonide In this example 1.1 equivalent of butyllithium in 25 ml. of hexane is added to a solution containing 0.5 g. of 3-[5-γ-cyclopentylpropylcarbonylaminothiazol-2-oxy]-propanediol 1,2-acetonide in 25 ml. of tetrahydrofuran at −78° C. Ten equivalents of methyl iodide is then added and the resulting mixture allowed to stand for 50 minutes and then refluxed for 5 hours. The mixture is then filtered, dried over sodium sulfate and evaporated to dryness affording a crude residue of 3-[5-N'-methyl-γ-cyclopentylpropylcarbonylaminothiazol-2-oxy]propanediol 1,2-acetonide which is then further purified by thin-layer chromatography.

Similarly by following the same procedure using the products of Example B as starting materials, the corresponding N'-methyl derivatives of the products of Example B are respectively prepared.

Similarly by following the same procedure but using in place of methyl chloride, the following compounds 5'-methylhexyl chloride, 4'-methylhexylbromide, phenyl bromide, γ-cyclopentylpropyl bromide, and ethyl iodo, the corresponding N'-methylhexyl, N'-phenyl, N-γ-cyclopentylpropyl and N-ethyl derivatives are respectively prepared.

EXAMPLE D 3-(5-γ-cyclopentylpropoxycarbonylaminothiazol-2-oxy)-propanediol 1,2-acetonide In this example 5.2 g. of 3-(5-azidocarbonylthiazol-2-oxy)-propanediol 1,2-acetonide is added to a mixture of 100 ml. of anhydrous toluene and 4 ml. of γ-cyclopentylpropanol. The resulting mixture is heated for one hour at 107° C and then the solvent distilled off under reduced pressure affording a crude residue of 3-(5-γ-cyclopentylpropoxycarbonylaminothiazol-2-oxy)-propanediol 1,2-acetonide which is then further purified by chromatography.

Similarly by following the same procedures using the corresponding substituted alcohol starting materials, the following compounds are respectively prepared:
3-(5-5'-methylhexoxycarbonylaminothiazol-2-oxy)-propanediol 1,2-acetonide;
3-(5-4'-methylhexoxycarbonylaminothiazol-2-oxy)-propanediol 1,2-acetonide;
3-(5-3'-methylhexoxycarbonylaminothiazol-2-oxy)-propanediol 1,2-acetonide;
3-(5-4'-methylhexoxycarbonylaminothiazol-2oxy)-propanediol 1,2-acetonide;
3-(5-4'-ethylhexoxycarbonylaminothiazol-2-oxy)-propanediol 1,2-acetonide;

3-(5-3'-propylhexoxycarbonylaminothiazol2-oxy)-propanediol 1,2-acetonide;

3-(5-n-heptoxycarbonylaminothiazol-2-oxy)-2-propanediol 1,2-acetonide;

3-(5-γ-cyclopentylpropoxycarbonylaminothiazol-2-oxy)-propanediol 1,2-acetonide;

3-(5-γ-cyclohexylpropoxycarbonylaminothiazol-2-oxy)-propanediol 1,2-acetonide;

3-(5-methoxycarbonylaminothiazol-2-oxy)-propanediol 1,2-acetonide;

3-(5-t-butoxycarbonylaminothiazol-2-oxy)-propanediol 1,2-acetonide;

3-(5-n-hexoxycarbonylaminothiazol-2-oxy)-propanediol 1,2-acetonide; and 3-(5-benzyloxycarbonylaminothiazol-2-oxy)-propanediol.

Similarly by following the same procedure but using the 4-position azidocarbonylthiazole isomer as starting material, the corresponding 4-position isomers of the above compounds are respectively prepared.

EXAMPLE E 3-(5-[N'-methyl-γ-cyclopentylpropoxycarbonylamino]-thiazol-2-oxy)-propanediol 1,2-acetonide.

In this example 1.1 equivalents of butyllithium in hexane is added to a solution containing 500 mg. of 3-(5-γ-cyclopentylpropoxycarbonylaminothiazol-2-oxy)-propanediol 1,2-acetonide in 25 ml. of tetrahydrofuran at −78° C. 10 equivalents of methyl iodide is then added and the resulting mixture allowed to stand for 50 minutes and then heated at reflux for 5 hours. The mixture is then filtered, dried over sodium sulfate and evaporated to dryness affording a crude residue of 3-(5-[N'-methyl-γ-cyclopentylpropoxycarbonylamino]-thiazol-2-oxy)-propanediol 1,2-acetonide which is then further purified by chromatography.

Similarly by following the same procedure using the products of Example D as starting materials, the corresponding N'-methyl derivatives of the products of Example D are respectively prepared.

Similarly by following the same procedure but using in place of methyl chloride, the following compounds 5'-methylhexyl chloride, 4 -methylhexyl bromide, phenyl bromide, γ-cyclopentylpropyl bromide, and ethyl iodo, the corresponding N'-methylhexyl, N'-phenyl, N'-γ-cyclopentylpropyl, and N'-ethyl derivatives are respectively prepared.

EXAMPLE F 3-(5-Formamidothiazol-2-oxy)-propanediol 1,2-acetonide

A solution containing 0.5 g. of 3-(5-isocyanatothiazol-2-oxy)-propanediol 1,2-acetonide in 20 ml. of 99.1% aqueous formic acid is heated at 80° C and monitored until thin-layer chromatographic analysis shows formation of the formyl derivative to be complete. The solvents are then removed by lyophilization and the residue dissolved in methylene dichloride. The methylene dichloride solution is washed with aqueous 1% sodium hydroxide solution and water, dried over sodium sulfate and evaporated to dryness yielding 3-(5-formamidothiazol-2-oxy)-propanediol. Similarly, 3-(4-formamidothiazol-2-oxy)-propanediol is prepared by the same procedure but using 3-(4-isocyanatothiazol-2-oxy)-propanediol 1,2-acetonide as starting material

EXAMPLE 1

In this example 10 g. of 2-bromo-5-ethoxycarbonylthiazole is stirred in 100 ml of anhydrous tetrahydrofuran, under a nitrogen atmosphere, and then 8.4 g. of a glycerol acetonide is added dropwise with stirring and the stirring continued until the solution is complete. The mixture is then cooled to −5° C and then 2.24 g. of sodium hydride (50% dispersion containing 2.24 g. of sodium hydride in mineral oil) in 100 ml. of anhydrous tetrahydrofuran is added and the resulting mixture allowed to warm to room temperature and allowed to stand for one half hour. The mixture is cooled to −10° C, resulting in the formation of a precipitate, and then poured into 200 ml. of ethyl acetate. The ethyl acetate mixture is washed three times with water, then dried over magnesium sulfate and evaporated to an oil which is then chromatographed on silica gel affording 3-(5-ethoxycarbonylthiazol-2-oxy)-propanediol 1,2-acetonide.

Similarly, by following the same procedure using the corresponding 2-bromo-4- or 5-alkoxycarbonylthiazole starting material, the corresponding compounds are respectively prepared:

3(4-ethoxycarbonylthiazol-2-oxy)-propanediol 1,2-acetonide;

3-(5-methoxycarbonylthiazol-2-oxy)-propanediol 1,2-acetonide; and 3-(4-methoxycarbonylthiazol-2-oxy)-propanediol 1,2-acetonide.

EXAMPLE 1A

This example illustrates methods according to the invention for preparing the intermediates of formula A wherein Z is

In this example a methanol solution containing 5 g. of 3-(5-ethoxycarbonylthiazol-2-oxy)-propanediol 1,2-acetonide; 20 ml. of water and 30 ml. of 4'-methylhexylamine and sufficient methanol to make the mixture homogeneous is stirred at room temperature for 18 hours, and then poured into 500 ml. of ethyl acetate. The ethyl acetate mixture is washed three times with water, dried over magnesium sulfate and evaporated to dryness affording a residue of 3-(5-4'-methylhexylaminocarbonylthiazol-2-oxy)-propanediol 1,2-acetonide which is then further purified by recrystallization using an ethyl-hexane mixture.

Similarly, by following the same procedure but respectively replacing 4'-methylhexylamine with the amines enumerated in Column A, the corresponding products of Column B are respectively prepared:

COLUMN A

3'-methylhexylamine;
5'-methylhexylamine;
4'-ethylhexylamine;
3'-propylhexylamine;
n-heptylamine;
β-cyclopentylethylamine;
γ-cyclopentylpropylamine;
4'-cyclopentylbutylamine;
γ-cyclohexylpropylamine;
5'-methyl-2'-methylhexylamine;

4'-methyl-1'-methylhexylamine;
γ-dimethylaminopropylamine;
6'-methylheptylamine;
5'-methylheptylamine;
N-(5'-methylhexyl)-N-methylamine;
N-(4'-methylhexyl)-N-methylamine;
6'-ethoxy-n-hexylamine;
n-hexylamine;
methylamine;
dimethylamine;
t-butylamine;
aqueous ammonia; and
benzylamine.

COLUMN B 3-(5-3'-methylhexylaminocarbonylthiazol-2-oxy)-propanediol 1,2-acetonide;

3-(5-5'-methylhexylaminocarbonylthiazol-2-oxy)-propanediol 1,2-acetonide;

3-(5-4'-ethylhexylaminocarbonylthiazol-2-oxy)-propanediol 1,2-acetonide;

3-(5-3'-propylhexylaminocarbonylthiazol-2-oxy)-propanediol 1,2-acetonide;

3-(5-n-heptylaminocarbonylthiazol-2-oxy)-propanediol 1,2-acetonide;

3-(5-β-cyclopentylethylaminocarbonylthiazol-2-oxy)-propanediol 1,2-acetonide;

3-(5-γ-cyclopentylpropylaminocarbonylthiazol-2-oxy)-propanediol 1,2-acetonide;

3-(5-4'-cyclopentylbutylaminocarbonylthiazol-2-oxy)-propanediol 1,2-acetonide;

3-(5-γ-cyclohexylpropylaminocarbonylthiazol-2-oxy)-propanediol 1,2-acetonide;

3-(5-5'-methyl-2'-methylhexylaminocarbonylthiazol-2-oxy)-propanediol 1,2-acetonide;

3-(5-4'-methyl-1'-methylhexylaminocarbonylthiazol-2-oxy)-propanediol 1,2-acetonide;

3-(5-γ-dimethylaminopropylaminocarbonylthiazol-2-oxy)-propanediol 1,2-acetonide;

3-(5-6'-methylheptylaminocarbonylthiazol-2-oxy)-propanediol 1,2-acetonide;

3-(5-5'-methylheptylaminocarbonylthiazol-2-oxy)-propanediol 1,2-acetonide;

3-(5-N-(5'-methylhexyl)-N-methylaminocarbonylthiazol-2-oxy)-propanediol 1,2-acetonide;

3-(5-N-(4'-methylhexyl)-n-methylaminocarbonylthiazol-2-oxy)-propanediol 1,2-acetonide;

3-(5-6'-ethoxy-n-hexylaminocarbonylthiazol-2-oxy)-propanediol 1,2-acetonide;

3-(5-hexylaminocarbonylthiazol-2-oxy)-propanediol 1,2-acetonide;

3-(5-methylaminocarbonylthiazol-2-oxy)-propanediol 1,2-acetonide;

3-(5-dimethylaminocarbonylthiazol-2-oxy)-propanediol 1,2-acetonide;

3-(5-t-butylaminocarbonylthiazol-2-oxy)-propanediol 1,2-acetonide;

3-(5-aminocarbonylthiazol-2-oxy)-propanediol 1,2-acetonide; and 3-(5-benzylaminocarbonylthiazol-2-oxy)-propanediol 1,2-acetonide.

Similarly, by following the same procedure but replacing 3-(5-ethoxycarbonylthiazol-2-oxy)-propanediol 1,2-acetonide with 3-(4-ethoxycarbonylthiazol-2-oxy)-propanediol 1,2-acetonide, the corresponding 4-position isomers of 3-(5-aminocarbonylthiazol-2-oxy)-propanediol 1,2-acetonide and of each of the products enumerated in Column B is respectively prepared.

EXAMPLE 1B

This example illustrates the preparation 4- and 5-aminocarbonyl starting materials of formula A. In this example sodium hydride (18 g., 56 wt. % dispersion in oil) is washed with n-hexane, and the hexane is replaced with monoglyme (100 ml.). To this mixture is added a solution of glycerol acetonide (44.5 g.) in monoglyme (200 ml.) under an atmosphere of nitrogen. After 15 minutes, 2-bromo-5-5'-methylhexylaminocarbonylthiazole (32 g.) is added, and the mixture is refluxed for 1.25 hours. The reaction mixture is then cooled, diluted with ether and filtered. The filtrate is washed with saturated aqueous sodium chloride solution twice, dried and concentrated by evaporation. Fractional distillation yields 3-(5'-methylhexylaminocarbonylthiazol-2-oxy)-propanediol 1,2-acetonide.

Similarly by following the same procedure but respectively replacing 2-bromo-5'-(5'-methylhexylaminocarbonyl)-thiazole with the compounds prepared in Preparations 2 and 4, the corresponding 3-(5- and 4-substituted aminocarbonylthiazol-2-oxy)-propanediol 1,2-acetonide compounds are respectively prepared.

EXAMPLE 2

This example illustrates methods according to step 1 of the generic process of the invention. In this example a mixture containing 2 g. of 3-(5-4'-methylhexylaminocarbonylthiazol-2-oxy)-propanediol 1,2-acetonide in 5 ml. of 80% aqueous formic acid is stirred at room temperature for 5 minutes. The solution is then evaporated under vacuum at room temperature affording a residue of 3-(5-4'-methylhexylaminocarbonylthiazol-2-oxy)-1,2-propanediol which is then further purified by recrystallization using an ethyl acetate-hexane mixture.

Similarly, by following the same procedure, the products prepared according to Examples 1A, 1B, and Examples B-E are respectively cleaved to the corresponding propanediol compounds.

EXAMPLE 3

This example illustrates steps 3 and 4 of the generic process of this invention and further illustrates preparation of the compounds of formula II of the invention. In this example 0.6 g. of methylsulfonyl chloride is added with rapid stirring to a mixture containing 1.2 g. of 3-(5-4'-methylhexylaminocarbonylthiazol-2-oxy)-propanediol in 20 ml. of pyridine at −30° C. The mixture is then allowed to warm to room temperature and evaporated to dryness affording a residue of 2-hydroxy-1-methylsulfonyloxy-3-(5-4'-methylhexylaminocarbonylthiazol-2-oxy)-propane. The residue is then dissolved in 50 ml. of anhydrous methanol and cooled to 0° C. A mixture containing 1 g. of sodium methoxide in 10 ml. of anhydrous methanol is added and the resulting mixture stirred for two minutes and then evaporated to remove methanol. 100 Milliliters of ethyl acetate is added and the resulting ethyl acetate mixture washed three times with water, dried over magnesium sulfate, and evaporated affording a residue of 1,2-epoxy-3-(5-4'-methylhexylaminocarbonylthiazol-2-oxy)-propane as an oily residue.

Similarly, by following the same procedure as above, the products, prepared according to Examples 2 and F, are converted to the corresponding 1,2-epoxypropane thiazole compounds of formula II.

EXAMPLE 4

This example illustrates further methods according to the invention of preparing the compounds of formula I to the invention. In this example 0.6 g. of isopropylamine is added to a solution containing 0.3 g. of 1,2-epoxy-3-(5-4'-methylhexylaminocarbonylthiazol-2-oxy)-propane in 20 ml. of anhydrous absolute ethanol, and then allowed to stand for 12 hours at room temperature. The mixture is then evaporated to dryness and the resulting residue chromatographed on silica gel yielding 1-isopropylamino-3-(5-4'-methylhexylaminocarbonylthiazol-2-oxy)-2-propanol.

Similarly, by following the above procedure but respectively using the products prepared according to Example 3 as starting materials, the corresponding compounds enumerated herein below are respectively prepared.

1-isopropylamino-3-(5-3'-methylhexylaminocarbonylthiazol-2-oxy)-2-propanol;
1-isopropylamino-3-(5-5'-methylhexylaminocarbonylthiazol-2-oxy)-2-propanol;
1-isopropylamino-3-(5-4'-ethylhexylaminocarbonylthiazol-2-oxy)-2-propanol;
1-isopropylamino-3-(5-3'-propylhexylaminocarbonylthiazol-2-oxy)-2-propanol;
1-isopropylamino-3-(5-n-heptylaminocarbonylthiazol-2-oxy)-2-propanol;
1-isopropylamino-3-(5-β-cyclopentylethylaminocarbonylthiazol-2-oxy)-2-propanol;
1-isopropylamino-3-(5-γ-cyclopentylpropylaminocarbonylthiazol-2-oxy)-2-propanol;
1-isopropylamino-3-(5-4'-cyclopentylbutylaminocarbonylthiazol-2-oxy)-2-propanol;
1-isopropylamino-3-(5-γ-cyclohexlpropylaminocarbonylthiazol-2-oxy)-2-propanol;
1-isopropylamino-3-(5-5'-methyl-2'-methylhexylaminocarbonylthiazol-2-oxy)-2-propanol;
1-isopropylamino-3-(5-4'-methyl-1'-methylhexylaminocarbonylthiazol-2-oxy)-2-propanol;
1-isopropylamino-3-(5γ-dimethylaminopropylaminocarbonylthiazol-2-oxy)-2-propanol;
1-isopropylamino-3-(5-6'-methhylheptylaminocarbonylthiazol-2-oxy)-2-propanol;
1-isopropylamino-3-(5-5'-methylheptylaminocarbonylthiazol-2-oxy)-2propanol;
1-isopropylamino-3-(5-N-(5'-methylhexyl)-N-methylaminocarbonylthiazol-2-oxy)-2propanol;
1-isopropylamino-3-(5-N-(4'-methylhexyl)-N-methylaminocarbonylthiazol-2-oxy)-2-propanol;
1-isopropylamino-3-(5-cyclopentylaminocarbonylthiazol-2-oxy)-2-propanol;
1-isopropylamino- 3-(5cycloheptylaminocarbonylthiazol-[2-oxy)-2-propanol;
1-isopropylamino-3-(5-n-octylaminocarbonylthiazol-2-oxy)-2-propanol;
1-isopropylamino-3-)5-n-nonylaminocarbonylthiazol-2-oxy)-2-propanol;
1-isopropylamino-3-(5-n-dodecylaminocarbonylthiazol-2-oxy)-2-propanol;
1-isopropylamino-3-(5-7'-hydroxyheptylaminocarbonyl-thiazol-2-oxy)-2-propanol;
1-isopropylamino-3-(5-9-acetoxynonylaminocarbonyl-thiazol-2-oxy)-2-propanol;
1-isopropylamino-3-(5-N,N-di(γ-cyclopentylpropyl)amino- aminocarbonylthiazol-2-oxy)-2-propanol;
1-isopropylamino-3-(5-N,N-di(n-dodccyl)aminocarbonylthiazol-2-oxy)-2-propanol;
1-isopropylamino-3-(5-4'-cyclopentybutylaminocarbonylthiazol-2-oxy)-2-propanol;
1-isopropylamino-3-(5-γ-cyclohexylpropylaminocarbonylthiazol-2-oxy)-2-propanol;
1-isopropylamino-3-(5-hexylaminocarbonylthiazol-2-oxy)-2-propanol;
1-isopropylamino -3-(5-methylaminocarbonylthiazol-2-oxy)-2-propanol;
1-isopropylamino-3-(5-dimethlaminocarbonylthiazol-2-oxy)-2-propanol;
1-isopropylamino-3-(5-t-butylaminocarbonylthiazol-2-oxy)-2-propanol;
1-isopropylamino-3-(5-aminocarbonylthiazol -2-oxy)-2-propanol;
1-isopropylamino-3-(5-benzylaminocarbonylthiazol -2-oxy)-2-propanol;
1-isopropylamino-3-(5-isopropylaminocarbonylthiazol-2-oxy)-2-propanol;
1-isopropylamino-3-(5-3'-methylhexylcarbonylaminothiazol-2-oxy)-2-propanol;
1-isopropylamino-3-(5-4'-methylhexylcarbonylaminothiazol-2-oxy)-2propanol;
1-isopropylamino-3-(5-5'-methylhexylcarbonylaminothiazol-2-oxy)-2-propanol;
1-isopropylamino-3-(5-4'-ethylhexylcarbonylaminothiazol-2-oxy)2-propanol;
1-isopropylamino-3-(5-3'-propylhexylcarbonylaminothiazol-2-oxy)-2-propanol;
1-isopropylamino-3-(5-n-heptylcarbonylaminothiazol-2-oxy)-2-propanol;
1-isopropylamino-3-(5-β-cyclopentylethylcarbonylaminothiazol -2-oxy)-2-propanol;
1-isopropylamino-3-(5-γ-cyclopentylpropylcarbonylaminothiazol -2-oxy)-2-propanol;
1-isopropylamino-3-(5-4'-cyclopentylbutylcarbonylaminothiazol -2-oxy)-2-propanol;
1-isopropylamino-3-(5-γ-cyclohexylpropylcarbonylaminothiazol -2-oxy)-2-propanol;
1-isopropylamino-3-(5-formamidothiazol-2-oxy)-2 -propanol;
1-isopropylamino-3-(5-methylcarbonylaminothiazol-2-oxy)-2-propanol;
1-isopropylamino-3-(5-t-butylcarbonylaminothiazol 2-oxy)-2-propanol;
1-isopropylamino-3-(5-n-hexylcarbonylaminothiazol -2-oxy)-2-propanol;
1-isopropylamino-3-(5-benzylcarbonylaminothiazol-2-oxy)- 2-propanol;
1-isopropylamino-3-(5-3'-methylhexoxycarbonylaminothiazol -2-oxy)-2-propanol;
1-isopropylamino-3-(5-4'-methylhexoxycarbonylaminothiazol -2-oxy)-2-propanol;
1-isopropylamino-3-(5-5'-methylhexoxycarbonylaminothiazol -2-oxy)-2-propanol;
1-isopropylamino-3-(5-4'-ethylhexoxycarbonylaminothiazol -2-oxy)-2-propanol;
1-isopropylamino-3-(5-3'-propylhexoxycarbonylaminothiazol -2-oxy)-2-propanol;
1-isopropylamino-3-(5-n-heptoxycarbonylaminothiazol- 2-oxy)-2-propanol;
1-isopropylamino-3-(5-βcyclopentylethoxycarbonylaminothiazol -2-oxy)-2propanol;
1-isopropylamino-3-(5-γ-cyclopentylpropoxycarbonylaminothiazol -2-oxy)-2-propanol;

1-isopropylamino-3-(5-4'-cyclopentylbutoxycarbonylaminothiazol -2-oxy)-2-propanol;

1-isopropylamino-3-(5-γ-cyclohexylproproxycarbonylaminothiazol -2-oxy)-2-propanol;

1-isopropylamino-3-(5-methoxycarbonylaminothiazol- 2-oxy)-2-propanol;

1-isopropylamino-3-(5-t-butoxycarbonylaminothiazol- 2-oxy)-2-propanol; and 1-isopropylamino-3-(5-hexoxycarbonylaminothiazol- 2-oxy)-2-propanol; and 1-isopropylamino-3-(5-benzyloxycarbonylaminothiazol- 2-oxy)-2-propanol.

Similarly the corresponding N'-substituted compounds of formula I (Z is

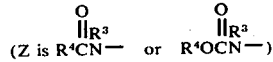
(Z is $R^4CN-$ or $R^4OCN-$)

corresponding to the starting materials prepared according to Examples C and E, are also respectively prepared but have not been enumerated above for purposes of brevity.

The 4-position isomers are similarly prepared according to the same procedure but using the corresponding 4-position isomer starting materials.

The hydrochloride addition salts of each of the above product compounds are then prepared by respectively treating 1 g. of each compound with one molar equivalent and 50 ml. of ethyl ether saturated with anhydrous gaseous hydrogen chloride at 20° C for 1 hour.

Similarly, by following the same procedure as above but using t-butylamine in place of isopropylamine, the corresponding 1-t-butylamine derivatives of each of the above products and also their hydrochloride addition salts are respectively prepared.

EXAMPLE 5

This example illustrates methods according to the invention of converting the compounds of formula II to the corresponding compounds of formula I of the invention. In this example, 350 mg. of 1,2-epoxy-3-(5-4'-methylhexylaminocarbonylthiazol -2-oxy)-propane is dissolved in 6 ml. of anhydrous ethanol saturated with ammonia and allowed to stand at room temperature for 20 hours. The mixture is then evaporated to remove ethanol and the resulting residue purified by thin-layer chromatography on preparative silica plates using a developing system of 1% triethylamine, 1.5% methanol and the remainder ethyl acetate, yielding 1-amino-3-(5-4'-methylhexylaminocarbonylthiazol-2-oxy)-propanol.

Similarly, by following the above procedure but respectively using the products, prepared according to Example 3, as starting materials, the corresponding 1-amino-3-(5 -substituted thiazol-2-oxy)-2-propanol compounds are respectively prepared.

Similarily by following the same procedure but replacing ammonia with methylamine, dimethylamine and ethylamine, respectively, the corresponding 1-methylamino; 1-dimethylamino; and 1-ethylamino derivatives are respectively prepared.

EXAMPLE 6

This example illustrates further methods according to the invention of preparing the compounds of formula I to the invention. In this example 1 g. of morpholine is added to a solution containing 0.3 g. of 1,2-epoxy-3-(5-4'-methylhexylaminocarbonylthiazol -2-oxy)-propane in 20 ml. of anhydrous absolute ethanol at 20° C. The resulting mixture is monitored by thin-layer chromatographic analysis and allowed to stand until conversion of the 1,2-epoxy-3-(5-aminocarbonylthiazol -2-oxy)-propane is essentially complete. The mixture is then evaporated to dryness yielding a crude residue of 1-(N-morpholino-3-(5-4'-methylhexylaminocarbonylthiazol-2-oxy)-2-propanol which is then further purified by thin-layer chromatography on silica gel.

Similarly, by following the same procedure as above but respectively using the products of Example 3 as starting materials, the corresponding 1-(N-morpholino)-3-(5-substituted aminocarbonylthiazol-2-oxy)-2-propanol derivatives are prepared.

The corresponding hydrochloride addition salts of each of the above products are respectively prepared by respectively treating the corresponding 1-(N-morpholino) derivatives, enumerated above, with hydrogen chloride as described in Example 4.

Similarly, by following the same procedure but respectively using pyrrolidine, piperidine, piperazine, N-β-hydroxyethylpiperazine, in place of morpholine, the corresponding 1-(N-pyrrolidinyl), 1-(N-piperidinyl), 1-(N-piperazinyl), and 1-[N-(N'-β-hydroxyethylpiperazinyl derivatives and their hydrochloride addition salts are respectively prepared for each of the above products using the respective products of Example 3 as starting materials.

The 4-position isomers are similarly prepared according to the same procedure but using the corresponding 4-position isomer starting materials.

EXAMPLE 7

This example illustrates further methods according to the invention of preparing further compounds of formula I of the invention. In this example 1 g. of β-(4-aminocarbonylphenoxy)-ethylamine (Cox et al, J. Med. Chem., v. 16, No. 11 (1973) is added to a solution containing 0.4 g. of 1,2-epoxy-3-(5-4'-methylhexylaminocarbonylthiazol-2-oxy)-propane in 20 ml. of anhydrous absolute ethanol at 20° C. The resulting mixture is monitored by thin-layer chromatographic analysis and allowed to stand until conversion of the 1,2-epoxy-3-(5-4'-methylhexylaminocarbonylthiazol-2-oxy)-propane is essentially complete. The mixture is then evaporated to dryness yielding a crude residue which is then further purified by thin-layer chromatography on silica gel yielding 1-[β-(4-aminocarbonylphenoxy)-ethylamino]-3-(5-4'-methylhexylaminocarbonylthiazol-2-oxy)-2-propanol.

Similarly, by following the same procedure but using the products of Example 3 as starting materials, the corresponding products enumerated herein below in Column E are respectively prepared:

COLUMN E

1-[β-(4-aminocarbonylphenoxy)-ethylamino]-3-(5-3'-methylhexylaminocarbonylthiazol-2-oxy)-2-propanol;

1-[β-(4-aminocarbonylphenoxy)-ethylamino]-3-(5-5'-methylhexylaminocarbonylthiazol-2-oxy)-2-propanol;

1-[β-(4-aminocarbonylphenoxy)-ethylamino]-3-(5-4'-ethylhexylaminocarbonylthiazol-2-oxy)-2-propanol;

1-[β-(4-aminocarbonylphenoxyl)-ethylamino]-3-(5-3'-propylhexylaminocarbonylthiazol-2-oxy)-2-propanol;

1-[β-(4-aminocarbonylphenoxy)-ethylamino]-3-(5-n-heptylaminocarbonylthiazol-2-oxy)-2-propanol;

1-[β-(4-aminocarbonylphenoxy)-ethylamino]-3-(5-β-cyclopentylethylaminocarbonylthiazol-2-oxy)-2-propanol;

1-[β-(4-aminocarbonylphenoxy)-ethylamino]-3-(5-γ-cyclopentylpropylaminocarbonylthiazol-2-oxy)-2-propanol;

1-[β-(4-aminocarbonylphenoxy)-ethylamino]-3-(5-4'-cyclopentylbutylaminocarbonylthiazol-2-oxy)-2-propanol;

1-[β-(4-aminocarbonylphenoxy)-ethylamino]-3-(5-γ-cyclohexylpropylaminocarbonylthiazol-2-oxy)-2-propanol;

1-[β-(4-aminocarbonylphenoxy)-ethylamino]-3-(5-5'-methyl-2'-methylhexylaminocarbonylthiazol-2-oxy)-2-propanol;

1-[β-(4-aminocarbonylphenoxy)-ethylamino]-3-(5-4'-methyl-1'-methylhexylaminocarbonylthiazol-2-oxy)-2-propanol;

1-[β-(4-aminocarbonylphenoxy)-ethylamino]-3-(5-γ-dimethylaminopropylaminocarbonylthiazol-2-oxy)-2-propanol;

1-[β-(4-aminocarbonylphenoxy)-ethylamino]-3-(5-6'-methylheptylaminocarbonylthiazol-2-oxy)-2-propanol;

1-[β-(4-aminocarbonylphenoxy)-ethylamino]-3-(5-5'-methylheptylaminocarbonylthiazol-2-oxy)-2-propanol;

1-[β-(4-aminocarbonylphenoxy)-ethylamino]-3-(5-N-(5'-methylhexyl)-N-methylaminocarbonylthiazol-2-oxy)-2-propanol;

1-[β-(4-aminocarbonylphenoxy)-ethylamino]-3-(5-cyclopentylaminocarbonylthiazol-2-oxy)-2-propanol;

1-[β-(4-aminocarbonylphenoxy)-ethylamino]-3-(5-cycloheptylaminocarbonylthiazol-2-oxy)-2-propanol;

1-[β-(4-aminocarbonylphenoxy)-ethylamino]-3-(5-n-octylaminocarbonylthiazol-2-oxy)-2-propanol;

1-[β-(4-aminocarbonylphenoxy)-ethylamino]-3-(5-n-nonylaminocarbonylthiazol-2-oxy)-2-propanol;

1-[β-(4-aminocarbonylphenoxy)-ethylamino]-3-(5-n-dodecylaminocarbonylthiazol-2-oxy)-2-propanol;

1-[β-(4-aminocarbonylphenoxy)-ethylamino]-3-(5-7'-hydroxyheptylaminocarbonylthiazol-2-oxy)-2-propanol;

1-[β-(4-aminocarbonylphenoxy)-ethylamino]-3-(5-9-acetoxynonylaminocarbonylthiazol-2-oxy)-2-propanol;

1-[β-(4-aminocarbonylphenoxy)-ethylamino]-3-(5-N,N-di(γ-cyclopentylpropyl)aminocarbonylthiazol-2-oxy)-2-propanol;

1-[β-(4-aminocarbonylphenoxy)-ethylamino]-3-(5-N,N-di(n-dodecyl)aminocarbonylthiazol-2-propanol;

1-[β-(4-aminocarbonylphenoxy)-ethylamino]-3-(5-4'-cyclopentylbutylaminocarbonylthiazol-2-oxy)-2-propanol; 1-[β-(4-aminocarbonylphenoxy)-ethylamino]-3-(5-γ-cyclohexylpropylaminocarbonylthiazol-2-oxy)-2-propanol;

1-[β-(4-aminocarbonylphenoxy)-ethylamino]-3-(5-hexylaminocarbonylthiazol-2-oxy)-2-propanol;

1-[β-(4-aminocarbonylphenoxy)-ethylamino]-3-(5-methylaminocarbonylthiazol-2-oxy)-2-propanol;

1-[β-(4-aminocarbonylphenoxy)-ethylamino]-3-(5-t-butylaminocarbonylthiazol-2-oxy)-2-propanol;

1-[β-(4-aminocarbonylphenoxy)-ehtylamino]-3-(5-aminocarbonylthiazol-2-oxy)-2-propanol;

1-[β-(4-aminocarbonylphenoxy)-ethylamino]-3-(5-benzylaminocarbonylthiazol-2-oxy)-2-propanol;

1-[β-(4-aminocarbonylphenoxy)-ethylamino]-3-(5-isopropylaminocarbonylthiazol-2-oxy)-2-propanol;

1-[β-(4-aminocarbonylphenoxy)-ethylamino]-3-(5-3'-methylhexylcarbonylaminothiazol-2-oxy)-2-propanol;

1-[β-(4-aminocarbonylphenoxy)-ethylamino]-3-(5-4'-methylhexylcarbonylaminothiazol-2-oxy)-2-propanol;

1-[β-(4-aminocarbonylphenoxy)-ethylamino]-3-(5-5'-methylhexylcarbonylaminothiazol-2-oxy)-2-propanol;

1-[β-(4-aminocarbonylphenoxy)-ethylamino]-3-(5-4'-ethylhexylcarbonylaminothiazol-2-oxy)-2-propanol;

1-[β-(4-aminocarbonylphenoxy)-ethylamino]-3-(5-3'-propylhexylcarbonylaminothiazol-2-oxy)-2-propanol;

1-[β-(4-aminocarbonylphenoxy)-ethylamino]-3-(5-n-heptylcarbonylaminothiazol-2-oxy)-2-propanol;

1-[β-(4-aminocarbonylphenoxy)-ethylamino]-3-(5-β-cyclopentylethylcarbonylaminothiazol-2-oxy)-2-propanol;

1-[β-(4-aminocarbonylphenoxy)-ethylamino]-3-(5-γ-cyclopentylpropylcarbonylaminothiazol-2-oxy)-2-propanol;

1-[β-(4-aminocarbonylphenoxy)-ethylamino]-3-(5-4'-cyclopentylbutylcarbonylaminothiazol-2-oxy)-2-propanol;

1-[β-(4-aminocarbonylphenoxy)-ethylamino]-3-(5-γ-cyclohexylpropylcarbonylaminothiazol-2-oxy)-2-propanol;

1-[β-(4-aminocarbonylphenoxy)-ethylamino]-3-(5-formamidothiazol-2-oxy)-2-propanol;

1-[β-(4-aminocarbonylphenoxy)-ethylamino]-3-(5-methylcarbonylaminothiazol-2-oxy)-2-propanol; 1-[β-(4-aminocarbonylphenoxy)-ethylamino]-3-(5-t-butylcarbonylaminothiazol-2-oxy)-2-propanol;

1-[β-(4-aminocarbonylphenoxy)-ethylamino]-3-(5-hexylcarbonylaminothiazol-2-oxy)-2-propanol;

1-[β-(4-aminocarbonylphenoxy)-ethylamino]-3-(5-benzylcarbonylaminothiazol-2-oxy)-2-propanol;

1-[β-(4-aminocarbonylphenoxyl)-ethylamino]-3-(5-3'-methylhexoxycarbonylaminothiazol-2-oxy)-2-propanol;

1-[β-(4-aminocarbonylphenoxy)-ethylamino]-3-(5-4'-methylhexoxycarbonylaminothiazol-2-oxy)-2-propanol;

1-[β-(4-aminocarbonylphenoxy)-ethylamino]-3-(5-5'-methylhexoxycarbonylaminothiazol-2-oxy)-2-propanol;

1-[β-(4-aminocarbonylphenoxy)-ethylamino]-3-(5-4'-ethylhexoxycarbonylaminothiazol-2-oxy)-2-propanol;

1-[β-(4-aminocarbonylphenoxy)-ethylamino]-3-(5-3'-propylhexoxycarbonylthiazol-2-oxy)-2-propanol;

1-[β-(4-aminocarbonylphenoxy)-ethylamino]-3-(5-n-heptoxycarbonylaminothiazol-2-oxy)-2-propanol;

1-[β-(4-aminocarbonylphenoxy)-ethylamino]-3-(5-β-cyclopentylethoxycarbonylaminothiazol-2-oxy)-2-propanol;

1-[β-(4-aminocarbonylphenoxy)-ethylamino]-3-(5-γ-cyclopentylpropoxycarbonylaminothiazol-2-oxy)-2-propanol;

1-[β-(4-aminocarbonylphenoxy)-ethylamino]-3-(5-4'-cyclopentylbutoxycarbonylaminothiazol-2-oxy)-2-propanol;

1-[β-(4-aminocarbonylphenoxy)-ethylamino]-3-(5-γ-cyclohexylpropoxycarbonylaminothiazol-2-oxy)-2-propanol;

1-[β-(4-aminocarbonylphenoxy)-ethylamino]-3-(5-methoxycarbonylaminothiazol-2-oxy)-2-propanol;

1-[β-(4-aminocarbonylphenoxy)-ethylamino]-3-(5-t-butoxycarbonylaminothiazol-2-oxy)-2-propanol;

1-[β-(4-aminocarbonylphenoxy)-ethylamino]-3-(5-hexoxycarbonylaminothiazol-2-oxy)-2-propanol; and 1-[β-(4-aminocarbonylphenoxy)-ethylamino]-3-(5-benzyloxycarbonylaminothiazol-2-oxy)-2-propanol.

Similarly the corresponding N'-substituted compounds of formula I (Z is

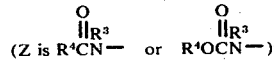
(Z is R⁴CN— or R⁴OCN—)

corresponding to the representative starting materials preferred according to Examples C and E are also respectively prepared but have not been enumerated above for purposes of brevity.

Similarly, by following the same procedure described as in Example 4, the hydrochloride addition salts of each of the above compounds are respectively prepared.

Similarly, by following the same procedure but respectively using ethanolamine; 1-amino-1-phenylethane; β-(p-hydroxyphenyl)-ethylamine; α-methyl-β-(p-hydroxyphenyl)-ethylamine; γ-(p-hydroxyphenyl)-propylamine; and α-methyl-γ-(4-hydroxyphenyl)-propylamine in place of β-(4-aminocarbonylphenoxy)-ethylamine, the corresponding 1-(β-hydroxy ethylamino)-; 1-(α-phenethylamino)-; 1-(β-[p-hydroxyphenyl]-ethylamino-; 1-(α-methyl-β-[p-hydroxyphenyl]-ethylamino)-; 1-(γ-(p-hydroxyphenyl)-propylamino)- and 1-(α-methyl-γ-[4-hydroxyphenyl]-propylamino- derivatives of the above enumerated products and their hydrochloride addition salts are respectively prepared.

The 4-position isomers are similarly prepared according to the same procedure but using the corresponding 4-position isomer starting materials.

EXAMPLE 8

This example illustrates the preparation of the oxazolidine reagent according to steps 1' and 2' of the process of the invention for preparing the 5- or

series of compounds of formula III. In this example 25 ml. of racemic glycidol and 50 ml. of t-butylamine are mixed together at room temperature. After about 30 minutes the mixture boils spontaneously and is then allowed to stand at room temperature for an additional 20 hours. The reaction mixture is then concentrated via evaporation to a vascous oil which is then dissolved in a solution containing 250 ml. of ethanol and 50 ml. of 37% (wt.) aqueous formaldehyde. The resulting mixture is refluxed for 18 hours and then evaporated, under vacuum, affording 5-hydroxymethyl-N-t-butyloxazolidine which is then further purified by distillation. Similarly, by following the same procedure but replacing t-butylamine with anhydrous ammonia, methylamine, isopropylamine, benzylamine, and α-methyl-γ-phenylpropylamine, respectively, the following compounds are respectively prepared:

5-hydroxymethyloxazolidine;

5-hydroxymethyl-N-methyloxazolidine;
5-hydroxymethyl-N-isopropyloxazolidine;
5-hydroxymethyl-N-benzyloxazolidine; and
5-hydroxymethyl-N-(α-[α-methyl-γ-phenylpropyl])-oxa zolidine. Also in he case of the volatile reagents (i.e. ammonia and methylamine), the procedure is conducted in a closed system by first bubbling the requisite amount of ammonia or methylamine through the glycidol and then sealing the reaction vessel.

EXAMPLE 9

This example illustrates methods according to the invention of preparing the compounds of formula I of the invention via the intermediate of formfula III of the invention. In this example 20 ml. of 5-hydroxymethyl-N-t-butyloxazolidine is added dropwise, with stirring, to a mixture containing 0.6 g. of sodium hydride (50% sodium hydride dispersed in mineral oil containing 26 g. sodium hydride) in 20 ml. of anhydrous tetrahydrofuran at room temperature under a nitrogen atmosphere. The mixture is stirred for 30 minutes and then a solution containing 3 g. of 2-bromo-5-5'-methylhexylaminocarbonylthiazole in 10 ml. of anhydrous tetrahydrofuran is added. The tetrahydrofuran is removed by evaporation under vacuum and the resulting concentrate stirred for 18 hours at room temperature and then poured into 200 ml. of ethyl acetate. The resulting ethyl acetate mixture is washed three times with water, and then dried over magnesium sulfate and evaporated to an oily residue. The oil is then distilled under vacuum to remove excess 5-hydroxymethyl-n-t-butyloxazolidine, and then chromatographed on silica gel yielding 1-t-butylamino-3-(5-5'-methylhexylamino-thiazol-2-oxy)-propanol.

Similarly, by following the same procedure but respectively using the corresponding 2-bromo-thiazole derivatives, prepared according to Preparations 2 or 4 starting materials, the following compounds ar respectively prepared:

COLUMN F 1-t-butylamino-3-(5-4'-methylhexylaminocarbonyl-thiazol-2-oxy)-2-propanol;

1-t-butylamino-3-(5-4'-methylhexylaminocarbonyl-thiazol-2-oxy)-2-propanol;

1-t-butylamino-3-(5-4'-ethylhexylaminocarbonyl-thiazol -2-oxy)-2-propanol;

1-t-butylamino-3-(5-3'-propylhexylaminocarbonyl-thiazol -2-oxy)-2-propanol;

1-t-butylamino-3-(5-β-cyclopentylethylaminocar-bonylthiazol-2-oxy) -2-propanol;

1-t-butylamino-3-(5-γ-cyclopentylpropylaminocar-bonylthiazol -2-oxy)-2-propanol;

1-t-butylamino-3-(5-n-heptylaminocarbonylthiazol-2-oxy)-2-propanol;

1-t-butylamino-3-(5-4'-cyclopentylbutylaminocar-bonylthiazol -2-oxy)-2-propanol;

1-t-butylamino-3-(5-γ-cyclohexylpropylaminocar-bonylthiazol -2-oxy)-2-propanol;

1-t-butylamino-3-(5-5'-methyl-2'-methylhex-ylaminocarbonylthiazol- 2-oxy)-2-propanol;

1-butylamino-3-(5-4'-methyl-1'-methylhex-ylaminocarbonylthiazol- 2-oxy)-2-propanol;

1-t-butylamino-3-(5-γ-dimethylamino-propylaminocarbonylthiazol -2-oxy)-2-porpanol;

1-t-butylamino-3-(5-6'-methylheptylaminocarbonyl-thiazol -2-oxy)-2-propanol;

1-t-butylamino-3-(5-5'-methylheptylaminocarbonyl-thiazol-2-oxy)-2-propanol;

1-t-butylamino-3-(5-N-(5'-methylhexyl)-N-methylaminocarbonylthiazol-2-oxy)-2-propanol;

1-t-butylamino-3-(5-N-(4'-methylhexyl)-N-methylaminocarbonylthiazol-2-oxy)-2-propanol;

1-t-butylamino-3-(5-cyclopentylaminocarbonyl-thiazol 2-oxy)-2-propanol;

1-t-butylamino-3-(5-cycloheptylaminocarbonyl-thiazol 2-oxy)-2-propanol;

1-t-butylamino-3-(5-n-octylaminocarbonylthiazol-2-oxy)-2-propanol;

1-t-butylamino-3-(5-n-nonylaminocarbonylthiazol-2-oxy)-2-propanol;

1-t-butylamino-3-(5-n-dodecylaminocarbonyl-thiazol-2-oxy)-2-propanol;

1-t-butylamino-3-(5-7'-hydroxyheptylaminocar-bonylthiazol-2-oxy)-2-propanol;

1-t-butylamino-3-(5-9-acetoxynonylaminocarbonyl-thiazol-2-oxy)-2-propanol;

1-t-butylamino-3-(5-N,N-di(γ-cyclopentylpropyl)aminocarbonylthiazol-2-oxy)-2-propanol;

1-t-butylamino-3-(5-N,N-di(n-dodecyl)aminocar-bonylthiazol-2-oxy)-2-propanol;

1-t-butylamino-3-(5-4'-cyclopentylbutylaminocar-bonylthiazol-2-oxy)-2-propanol;

1-t-butylamino-3-(5-γ-cyclohexylpropylaminocar-bonylthiazol-2-oxy)-2-propanol;

1-t-butylamino-3-(5-n-hexylaminocarbonylthiazol-2-oxy)-2-propanol;

1-t-butylamino-3-(5-methylaminocarbonylthiazol-2-oxy)-2-propanol;

1-t-butylamino-3-(5-dimethylaminocarbonylthiazol-2-oxy)-2-propanol;

1-t-butylamino-3-(5-isopropylaminocarbonylthiazol-2-oxy)-2-propanol;

1-t-butylamino-3-(5-aminocarbonylthiazol-2-oxy)-2-propanol; and 1-t-butylamino-3-(5-benzylaminocarbonylthiazol-2-oxy)2-propanol.

The 4-position isomers are similarly prepared according to the same procedure but using the corresponding 4-position isomer starting materials.

Similarly, but following the same procedure but respectively using 5-hydroxymethyloxazolidine; 5-hydroxymethyl-N-methyloxazolidine; 5-hydroxymethyl-N-isopropyloxazolidine; 5-hydroxymethyl-N-benzyloxazolidine; and 5-hydroxmethyl-N-(α-[α-methyl-γ-phenylpropyl]) -oxazolidine in place of 5-hydroxymethyl-N-t-butyloxazolidine as starting materials, the corresponding 1-amino-; 1-methylamino-; 1-isopropylamino-; 1-benzylamino-; and 1-(α-methyl-β-phenethyl)-amino-derivatives of each of the above products are respectively prepared.

EXAMPLE 10

This example illustrates methods according to the invention of preparing the compounds of formula III of the invention. In this example 3.0 g. of 5-hydroxymethyl-N-(α-)-oxazolidine in 10ml. of anhydrous dimethylformamide is added to a susspension containing 0.9 g. of sodium hydride in 8 ml. of dimethylformamide under a nitrogen atmosphere. The resulting mixture is heated at 80°C for 15 minutes and then cooled to room temperature and 2.5 g. of 2-bromo-5-5'-methylhex-ylaminocarbonylthiazole in 15 ml. of anhydrous dimethylformamide is added. The resulting mixture is heated at 80° C for 2 hours, then cooled to room temperature and evaporated under high vacuum to yield, as a residue, 5-(5-5'-methylhexyl-t-butylaminocar-bonylthiazol-2-oxy)-methylene-N-(α-methyl-γ--phenylpropyl)-oxazolidine.

Similarly, by following the same procedure but respectively replacing 2-bromo-5-5'-methylhex-ylaminocarbonylthiazole with the corresponding 2-bromo-5-substituted aminocarbonylthiazole compounds, prepared according to Preparation 2, the corresponding oxazolidine derivatives of formula III are respectively prepared.

Similarly, by following the same procedure but respectively replacing 5-hydroxymethyl-N-(α-)-oxazolidine; 5-hydroxymethyl-N-t-butyloxazolidine; 5-hydroxymethyloxazolidine; 5-hydroxymethyl-N-methyloxazolidine; 5-hydroxymethyl-N-isopropyloxazolidine; and 5-hydroxymethyl-N-benzyloxazolidine, the corresponding N-t-butyloxazolidine; oxazolidine; N-methyloxazolidine; N-isopropyloxazolidine; and N-benzyloxazolidine derivatives of each of the above products are respectively prepared.

The 4-position isomers are similarly prepared according to the same procedure but using the corresponding 4-position isomer starting materials prepared according to Preparation 2.

EXAMPLE 11

This example illustrates methods of converting the compounds of formula III into the compounds of formula I of the invention. In this example 1 g. of 5-(5-5'-methylhexlaminocarbonylthiazol-2-oxy)-methylene-N-(α-methyl-γ-phenylpropyl)-oxazolidine is dissolved in 50 ml. of ethyl acetate and this solution is washed three times with aqueous 5% sodium hydroxide (20 ml.) at 20° C. The mixture is allowed to stand for 0.5 hours, washed with water, dried over magnesium sulfate and then evaporated to dryness affording 1 -(α-methyl-γ-phenylpropylamino)-3-(5-5'-methylhexylaminocar-bonylthiazol -2-oxy)-2-propanol, which is then further purified by chromatography on silica gel plates.

Similarily, by following the same procedure using the oxazolidine products of formula III of Example 10, are hydrolyzed to the corresponding products of formula I.

EXAMPLE 12

This example illustrates an alternate method for converting compounds of formula III to compounds of formula I. In this example 1 g. of 5-(5-5'-methylhex-ylaminocarbonylthiazol -2-oxy)-methylene-N-t-butyloxazolidine is dissolved in 20 ml. of methanol containing 4 cc. of 5% aqueous hydrochloric acid at 20° C. After 15 minutes, the mixture is neutralized with dilute aqueous sodium carbonate solution, poured into water and extracted with ethyl acetate. The ethyl acetate extract is evaporated to dryness yielding 1-t-butylamino-3-(5-5'-methylhexylaminocarbonylthiazol -2-oxy) -2-propanol.

Similarly, by following the same procedure, the compounds of formula III, enumerated in Example 10, are respectively hydrolyzed to the corresponding compounds of formula I.

EXAMPLE 13

This example illustrates methods, according to the invention, of converting compounds of formula I into compounds of formula III of the invention. In this example 1 g. of 1-isopropylamino-3-(5-5'-methylhex-ylaminocarbonylthiazol -2-oxy)-2-propanol is dissolved in 25 ml. of acetone at 20° C, and 2 g. of aluminum isopropoxide is then added. The solution is stirred for four days at 20° C and then 50 ml. of hexane and 5 ml. of water are added and the resulting mixture is allowed to stand for 15 minutes. The resulting hexane phase is separated and then evaporated to dryness yielding 5-(5-5'-methylhexylaminocarbonylthiazol -2-oxy)-methylene-N-isopropyl-2,2-dimethyloxazolidine.

Similarly, by following the same procedure, the compounds of formula I, prepared in Examples 4 and 5, are respectively converted into the corresponding compounds of formula III.

Similarly, the corresponding thiazol- and 4- or 5-substituted thiazol-2-oxy-5-methylene-N-isopropyl-2-spiro- cyclohexyloxazolidine compounds of formula III are prepared according to the same procedure but using cyclohexanone in place of acetone.

EXAMPLE 14

This example illustrates further methods, according to the invention, of converting the compounds of formula I into the corresponding compounds of formula III. In this example 380 mg. of 1-t-butylamino-3-(5-5'-methylaminocarbonylthiazol -2-oxy)-2-propanol and a molar equivalent amount of cyclohexanone are dissolved in 15 ml. of ethyl ether at 20° C and 0.3 g. of anhydrous potassium carbonate is then added. The mixture is stirred for 18 hours at room temperature and then filtered. The filtrate is evaporated to dryness yielding 5-(5-5'-methylhexylaminocarbonylthiazol -2-oxy)-methylene-N-t-butyl-2-spiro-cyclo- oxazolidine.

Similarly, by following the same procedure, the products of formula I, of Examples 4 and 5, are respectively converted into the corresponding 2-spiro-cyclohexyloxazolidine compounds of formula III.

EXAMPLE 15

This example illustrates methods of preparing hydrochloride addition salts of the invention. In this example 1 g. of 1-t-butylamino-3-(5-5'-methylhexylaminocarbonylthiazol-2-oxy)-2-propanol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with ethyl ether and then crystallized from methanol, containing 1% water and 1 % acetone, affording crystalline 1-t-butylamino- 3 -(5-5'-methylehexylaminocarbonylthiazol-2-oxy)-2-propanol hydrochloride.

Similarly, by following the same procedure using each of the compounds of formula I, prepared according to Examples 4-7, 9, 11 and 12 and the compounds of formula III, prepared according to Examples 10, 13 and 14 as starting materials, the corresponding hydrochloride addition salts of each of these compounds is respectively prepared.

EXAMPLE 16

This example illustrates methods of preparing the maleate addition salts of compounds of formulas I and III. In this example one gram of 1-t-butylamino-3-(5-5'-methylhexylaminocarbonylthiazol -2 -oxy)-2-propanol is dissolved in a solution of 5 ml. of ethyl ether and 5 ml. of ethanol at 20° C. To this solution is added 10 ml. of a saturated solution of maleic acid in ethyl ether. The mixture is allowed to stand for 1 hour at room temperature. The resulting precipitate is recovered by filtration, washed three times with ethyl ether and then crystallized from a mixture of ethyl ether and ethanol (1:1 ) affording crystalline 1-t-butylamino-3-(5 -5'-methylhexylaminocarbonylthiazol -2-oxy)-2 -propanol maleate salt.

Similarly, by following the same procedure using each of the compounds of formula I, prepared according to Examples 4-7, 9, 11 and 12 and the compounds of formula III, prepared according to Examples 10, 13 and 14 as starting materials, the corresponding maleate addition salts of each of these compounds is respectively prepared.

EXAMPLE 17

This example illustrates the preparation, according to the invention, of the pure (+) optical isomers of the compounds of formulas I, II and III. In this example, the procedures of Preparation 5 and Examples A-F and 1- are repeated but in this instance, in place of racemic glycerol acetonide, the pure (+) optical isomer of glycerol acetonide is used as starting material in Preparation 5 and Examples 1 A and 1 B, and in the case of Example 8, the pure (+) optical isomer of glycerol is used in place of racemic glycerol.

EXAMPLE 18

This example illustrates the preparation, according to the invention, of the pure (−) optical isomers of the compounds of formulas I, II and III. In this example, the procedures of Preparation 5 and Examples A–F and 1–16 are repeated but in this instance, in place of racemic glycerol acetonide, the pure (−) optical isomer of glycerol acetonide is used as starting material in Preparation 5 and Examples 1 A and 1 B, and in the case of Example 8, the pure (−) optical isomer of glycerol is used in place of racemic glycerol.

Obviously many modifications and variations of the invention, described herein above and below in the Claims, can be made without departing from the essence and scope thereof.

What is claimed is:

1. A pharmaceutical compostion for treating cardiovascular disorders in mammals by blocking β-adrenergic receptor sites, comprising a pharmaceutically acceptable carrier and an effective amount of β-adrenergic blocking agent selected from the group of the compounds having the formula:

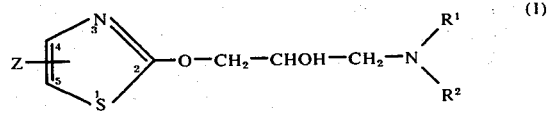

wherein $R^1$ and $R^2$ are independently selected from the group consisting of hydrogen; lower alkyl; cycloalkyl having from three through seven ring atoms; lower alkenyl; phenyl; phenyl lower alkyl wherein said alkyl has from one through six carbon atoms; substituted phenyl or substituted phenyl lower alkyl wherein said phenyl has one or two substituents independently selected from the group of hydroxy, lower alkyl, lower alkoxy and halo; and groups having the formulas

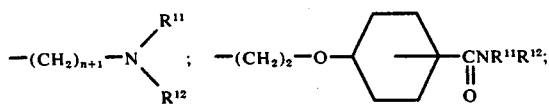

or —$(CH_2)_n$—Y' wherein n is a whole integer of from one through four; $R^{11}$ and $R^{12}$ are independently hydrogen or lower alkyl; and Y' is a heterocycle selected from the group of morpholino, pyrrolidinyl, piperidinyl, piperazinyl, N-lower alkylpiperazinyl or N'-hydroxy lower alkylpiperazinyl; or $R^1$ and $R^2$ together with the nitrogen atom to which they are joined form a nitrogen heterocycle selected from the group of morpholino, pyrrolidinyl, piperidinyl, piperazinyl, N'-lower alkylpiperazinyl or N'-hydroxy lower alkylpiperazinyl;

Z is a substituent on the thiazole ring at either the 4 - or 5 -position selected from the group having the formulas:

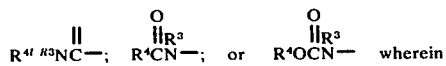 wherein wherein $R^3$ and $R^4$ are independently selected from the group of hydrogen; alkyl having from one through 12 carbon atoms; cycloalkyl having from three through 12 carbon atoms; phenyl; phenyl lower alkyl wherein said alkyl has from one through six carbon atoms; substituted phenyl or substituted phenyl lower alkyl wherein said phenyl has one or two substituents independently selected from the group of hydroxy, lower alkyl, lower alkoxy, or halo; terminally substituted alkyl group having from two through 12 carbon atoms having one substituted terminal carbon atom having a substituent selected from the group of hydroxy, acyloxy having from two through 12 carbon atoms and alkoxy having from one through six carbon atoms; and groups having the formulas - $(CH_2)_n\underset{+}{N}R^8R^9$ or - $(CH_nnR^{10}$ wherein n is a whole integer of from one through four, $R^8$ and $R^9$ are independently selected from the group of hydrogen and alkyl groups having from one through four carbon atoms and $R^{10}$ is cycloalkyl having from three through eight carbon atoms; and wherein when Z is

then $R^4$ cannot be hydrogen; a pharmaceutically acceptable salt of the compound of formula I; and mixtures thereof.

2. The composition of claim 27 wherein one of $R^1$ and $R^2$ is hydrogen and the other is selected from the group consisting of isopropyl; sec-butyl; t-butyl; cyclorpropyl; cyclopentyl; α-phenylethyl; β-hydroxyethyl; α-phenylpropyl; β-(3,4-dimethoxyphenyl)-ethyl; β-(4-hydroxyphenyl)-ethyl; α-methyl- β-(4-hydroxyphenyl)-ethyl; γ-(4-hydroxyphenyl)-propyl; α- methyl-γ-(4-hydroxyphenyl)-propyl; α-methyl-γ-phenylpropyl; and β-(4-aminocarbonylphenoxy)-ethyl.

3. The composition of claim 1 wherein $R^3$ is hydrogen and $R^4$ is selected from the group consisting of n-pentyl; n-hexyl; 3'- methylhexyl; 1'-methylhexyl; 4'-ethylhexyl; 3'-propylhexyl; n-heptyl; n-octyl; cycloheptyl; cyclohexyl; β-cyclopentyl- ethyl; γ-cyclopentylpropyl; 4'-cyclopentylbutyl; γ-cyclo- hexylpropyl; benzyl; β-methoxyethyl; γ-dimethylaminopropyl; 5'-methylhexyl; and 4'-methylhexyl.

4. The composition of claim 3 wherein one of $R^1$ and $R^2$ is hydrogen and the other is selected from the group consisting of isopropyl; sec-butyl; t-butyl; cyclopropyl; cyclopentyl; α-phenylethyl; β-hydroxyethyl; α-phenylpropyl; β-(3, 4-di- methoxyphenyl)-ethyl; β-(4-hydroxyphenyl)-ethyl; α-methyl- β-(4-hydroxyphenyl)-ethyl; γ-(4-hydroxyphenyl)-propyl; α- methyl-γ-(4-hydroxyphenyl)-propyl; α-methyl-γ-phenylpropyl; and β- (4-aminocarbonylphenoxy)-ethyl.

5. The composition of claim 3 wherein $R^4$ is selected from the group consisting of 5'-methylhexyl and 4'-methyl- hexyl.

6. The composition of claim 2 wherein said β-adrenergic blocking agent is selected from the group consisting of 1-t-butylamino-3-(5-5'- -methylhexylaminocarbonylthiazol-2-oxy)-2-propanol, a pharmaceutically acceptable salt thereof, and mixtures thereof.

* * * * *

UNITED STATES PATENT OFFICE
CERTIFICATE OF CORRECTION

Patent No. 4,001,421                    Dated January 4, 1977

Inventor(s) John A. Edwards

It is certified that error appears in the above-identified patent and that said Letters Patent are hereby corrected as shown below:

Column 1, line 33, "derivatives thereof" should read -- derivatives and/or substituted oxazolidine derivatives thereof --. Column 2, line 23, "whrein" should read -- wherein --. Column 3, line 10, "inventon" should read -- invention --. Column 4, lines 18 and 19, "substitute" should read -- substituted --. Column 5, line 10, "acitivty" should read -- activity --. Column 9, line 48, "pierato" should read -- picrate --. Column 11, line 11, "-ethylaminol]" should read -- -ethylamino] -- Column 12, line 35, "-γcyclohexylpropylcar-" should read -- -γ-cyclohexylpropylcar- --. Column 17, line 49, "exaple" should read -- example --. Column 18, lines 15-30, that portion of the formula reading:

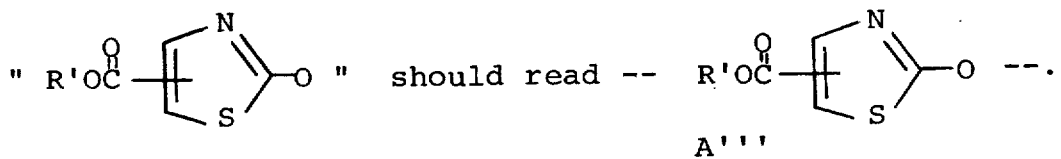

Column 19, line 11, "prefeably" should read -- preferably --. Column 22, lines 40-68, third formula,

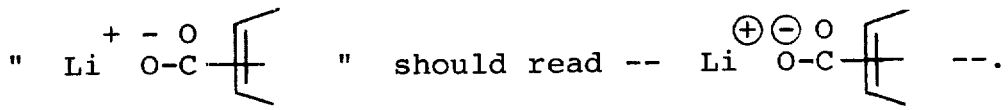

Column 33, line 8, "respectibely" should read -- respectively --. Column 34, line 26, "propenediol" should read -- propanediol --. Column 37, line 1, "-propylhexoxycarbonylaminothiazol2-" should read -- -propylhexoxycarbonylaminothiazol-2- --.

UNITED STATES PATENT OFFICE
CERTIFICATE OF CORRECTION

Patent No. 4,001,421　　　　　　　Dated January 4, 1977

Inventor(s) John A. Edwards

It is certified that error appears in the above-identified patent and that said Letters Patent are hereby corrected as shown below:

Column 41, line 52, "-2propanol;" should read -- -2-propanol; --.
Column 41, line 58, "thiazol-[2-oxy)" should read -- thiazol-2-oxy) --. Column 42, line 3, "-dodccyl)" should read -- -dodecyl) --. Column 42, line 26, "-2propanol;" should read -- -2-propanol; --. Column 42, line 65, "-βcyclopentylethoxycar-" should read -- -β-cyclopentylethoxycar- --. Column 42, line 66, "-2propanol;" should read -- -2-propanol; --. Column 43, line 14, "formula I (Z is" should read -- formula I --. Column 45, between lines 62 and 63, insert -- 1-[β-(4-aminocarbonylphenoxy)-ethylamino]-3-(5-dimethylaminocarbonylthiazol-2-oxy)-2-propanol --
Column 45, line 65, "-ehtylamino]-" should read -- -ethylamino]- --
Column 47, line 10, "formula I (Z is" should read -- formula I --.
Column 48, line 66, "-porpanol;" should read -- propanol; --.
Column 48, line 5, "he" should read -- the --. Column 48, line 15, "formfula" should read -- formula --. Column 49, line 40, "oxy)2-" should read -- oxy)-2- --. Column 49, line 59, "yl-N-(α-)-oxazolidine" should read -- yl-N-(α-[α-methyl-γ-phenylpropyl])-oxazolidine --. Column 50, line 13, "(α-)-" should read --(α-[α-methyl-γ-phenylpropyl])- --. Column 51, line 49, "methylehexylaminocarbonylthiazol" should read -- methylhexylaminocarbonylthiazol --. Column 52, line 20, "1- are" should read -- 1-16 are --. Column 53, line 1-7, that part of the formula reading:

" 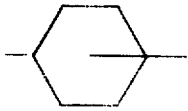 "　　　should read --　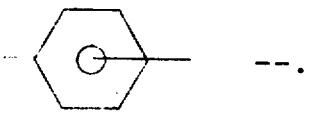　--.

UNITED STATES PATENT OFFICE
CERTIFICATE OF CORRECTION

Patent No. 4,001,421      Dated January 4, 1977

Inventor(s) John A. Edwards

It is certified that error appears in the above-identified patent and that said Letters Patent are hereby corrected as shown below:

Column 53, line 25, first formula:

"$R^{4\iota}\ R3_N\overset{\parallel}{C}-;$" should read -- $R^4R^3N\overset{O}{\overset{\parallel}{C}}-;$ --.

Column 53, line 42, "$(CH_n nR^{10}$" should read -- $(CH_2)_n R^{10}$ --.

Column 54, line 11, "claim 27" should read -- claim 1 --.

Column 54, line 13, "cyclor-" should read -- cyclo- --.

Signed and Sealed this

Sixth Day of June 1978

[SEAL]

Attest:

RUTH C. MASON
*Attesting Officer*

DONALD W. BANNER
*Commissioner of Patents and Trademarks*